United States Patent
Kasai et al.

(10) Patent No.: US 9,440,987 B2
(45) Date of Patent: *Sep. 13, 2016

(54) AROMATIC RING COMPOUND

(71) Applicant: TAKEDA PHARMACEUTICAL COMPANY LIMITED, Osaka (JP)

(72) Inventors: Shizuo Kasai, Kanagawa (JP); Hideyuki Igawa, Kanagawa (JP); Masashi Takahashi, Kanagawa (JP); Asato Kina, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/399,251

(22) PCT Filed: May 9, 2013

(86) PCT No.: PCT/JP2013/063029
§ 371 (c)(1),
(2) Date: Nov. 6, 2014

(87) PCT Pub. No.: WO2013/168759
PCT Pub. Date: Nov. 14, 2013

(65) Prior Publication Data
US 2015/0087672 A1    Mar. 26, 2015

Related U.S. Application Data

(60) Provisional application No. 61/645,164, filed on May 10, 2012.

(51) Int. Cl.
| | | |
|---|---|---|
| *A61P 43/00* | (2006.01) | |
| *C07D 519/00* | (2006.01) | |
| *C07D 491/048* | (2006.01) | |
| *A61P 3/04* | (2006.01) | |
| *A61K 31/4355* | (2006.01) | |

(52) U.S. Cl.
CPC ......... *C07D 491/048* (2013.01); *C07D 519/00* (2013.01)

(58) Field of Classification Search
CPC ............ C07D 519/00; C07D 491/048; A61K 31/4355
USPC .......................................... 514/302; 546/116
See application file for complete search history.

(56) References Cited

U.S. PATENT DOCUMENTS

| | | | |
|---|---|---|---|
| 2004/0077628 A1 | 4/2004 | Ishihara et al. | |
| 2006/0194871 A1* | 8/2006 | Barvian ............... | C07D 311/80 514/455 |
| 2007/0093508 A1* | 4/2007 | Ahmad et al. ............. | 514/260.1 |
| 2009/0233919 A1 | 9/2009 | Amegadzie et al. | |
| 2009/0264426 A1 | 10/2009 | Sakuraba et al. | |
| 2009/0318439 A1 | 12/2009 | Guzzo et al. | |
| 2010/0069362 A1 | 3/2010 | Murata | |
| 2012/0157460 A1* | 6/2012 | Surman et al. ............... | 514/250 |
| 2015/0018363 A1* | 1/2015 | Kasai et al. ............. | 514/252.04 |
| 2015/0018373 A1* | 1/2015 | Igawa et al. ............. | 514/255.05 |
| 2015/0111894 A1* | 4/2015 | Kasai et al. .................. | 514/248 |

FOREIGN PATENT DOCUMENTS

| | | | |
|---|---|---|---|
| WO | 01/82925 | | 11/2001 |
| WO | 2006/118320 | | 11/2006 |
| WO | WO 2007011285 | * | 1/2007 |
| WO | 2007/029847 | | 3/2007 |
| WO | 2008/086409 | | 7/2008 |
| WO | 2011/127643 | | 10/2011 |
| WO | 2011/130086 | | 10/2011 |
| WO | 2013/105676 | | 7/2013 |

OTHER PUBLICATIONS

Rivera; Current Medicinal Chemistry 2008, 15, 1025-1043.*
Carpenter; Bioorganic & Medicinal Chemistry Letters 2006, 16, 4994-5000.*
Tavares; J. Med. Chem. 2006, 49, 7108-7118.*
International Search Report issued Jul. 23, 2013 in International (PCT) Application No. PCT/JP2013/063029.
Surman et al., "5-(Pyridinon-1-yl)indazoles and 5-(furopyridinon-5-yl)indazoles as MCH-1 antagonists", Bioorganic & Medicinal Chemistry Letters, vol. 20, Sep. 2010, pp. 7015-7019.
Partial Supplementary European Search Report mailed Oct. 20, 2015 in corresponding European Patent Application No. 13786954.1.

* cited by examiner

*Primary Examiner* — Andrew D Kosar
*Assistant Examiner* — Daniel Carcanague
(74) *Attorney, Agent, or Firm* — Wenderoth, Lind & Ponack, L.L.P.

(57) ABSTRACT

The present invention provides an aromatic ring compound having a melanin-concentrating hormone receptor antagonistic action and useful as an agent for the prophylaxis or treatment of obesity and the like. The present invention relates to a compound represented by the formula (I)

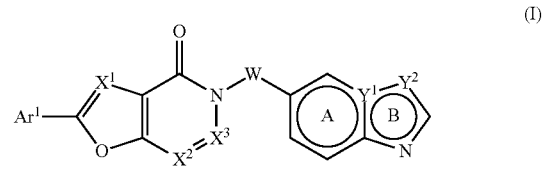

wherein each symbol as defined in the specification, or a salt thereof.

10 Claims, No Drawings

AROMATIC RING COMPOUND

TECHNICAL FIELD

The present invention relates to an aromatic ring compound having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food intake amount and a lighter body weight as compared to normal mouse (Nature, vol. 396, page 670, 1998). Furthermore, MCH receptor-1-deficient mice have been reported to show a lean phenotype (Proc. Natl. Acad. Sci. USA, vol. 99, page 3240, 2002). Therefrom MCH receptor (particularly MCH receptor 1) antagonists are expected to be superior appetite suppressants or anti-obesity agents.

As compounds having a MCH receptor antagonistic action, the following compounds are known.

1) WO2007/029847 (patent document 1) discloses a pyridone derivative represented by the formula:

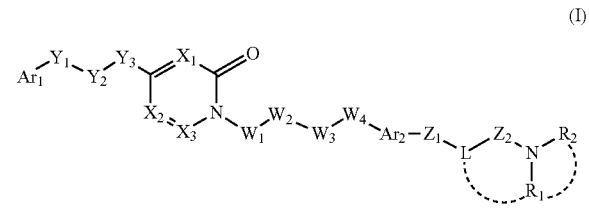

(I)

wherein $R_1$ and $R_2$ are the same or different and each is a hydrogen atom, a lower alkyl group optionally having substituent(s) or a lower cycloalkyl group optionally having substituent(s), or $R_1$ and $R_2$ form, together with the nitrogen atom bonded thereto, an aliphatic nitrogen-containing heterocycle optionally having substituent(s), $X_1$, $X_2$ and $X_3$ are the same or different and each is a methine group optionally having substituent(s) or a nitrogen atom, provided that $X_1$, $X_2$ and $X_3$ are not simultaneously nitrogen atoms, $Y_1$ is a single bond, —O—, —NR—, —S—, —SO— or —$SO_2$—, $Y_2$ is a lower alkylene group optionally having substituent(s), a lower alkenylene group optionally having substituent(s) or a lower cycloalkylene group optionally having substituent(s), $Y_3$ is a single bond, —O—, —NR—, —S—, —SO— or —$SO_2$—, each R is independently a hydrogen atom or a lower alkyl group optionally having substituent(s), $W_1$, $W_2$, $W_3$ and $W_4$ are the same or different and each is a single bond, a methylene group optionally having substituent(s) or —O—, provided that continuous two or more of $W_1$, $W_2$, $W_3$ and $W_4$ are not simultaneously —O—, L is a single bond, a methylene group optionally having substituent(s) or an ethylene group optionally having substituent(s), and L optionally forms, together with $Z_2$, $R_1$ and the nitrogen atom bonded to $R_2$, an aliphatic nitrogen-containing heterocycle optionally having substituent(s), $Z_1$ and $Z_2$ are the same or different, and each is a single bond, a $C_{1-4}$ alkylene group optionally having substituent(s) or —O—, $Ar_1$ is an aromatic carbocyclic group optionally having substituent(s) or an aromatic heterocyclic group optionally having substituent(s), and $Ar_2$ is a divalent and bicyclic aromatic carbocyclic group optionally having substituent(s) or a divalent and bicyclic aromatic heterocyclic group optionally having substituent(s), or a pharmaceutically acceptable salt thereof.

2) WO2008/086409 (patent document 2) discloses a compound represented by the following formula:

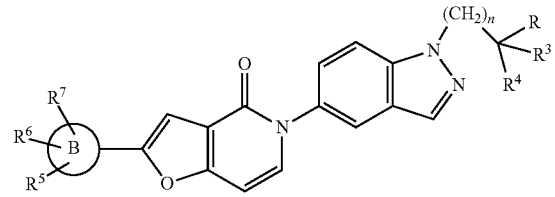

wherein n is 1 or 2,

R is $NR^1R^2$, wherein $R^1$ and $R^2$ are each independently selected from H and optionally substituted alkyl, or $R^1$ and $R^2$ form, together with the adjacent N atom, a 4- to 7-membered optionally substituted heterocycle optionally containing 1 or 2 hetero atoms in addition to the N atom shown, $R^3$ and $R^4$ are each independently selected from H and alkyl, or R, $R^3$ and $R^4$ may combine to form an optionally substituted imidazolin-2-yl, B is aryl or heteroaryl, and $R^5$, $R^6$ and $R^7$ are each independently selected from H, —OH, —O— alkyl, alkyl, halo, —$CF_3$ and —CN, provided the aforementioned compound is not any of the following

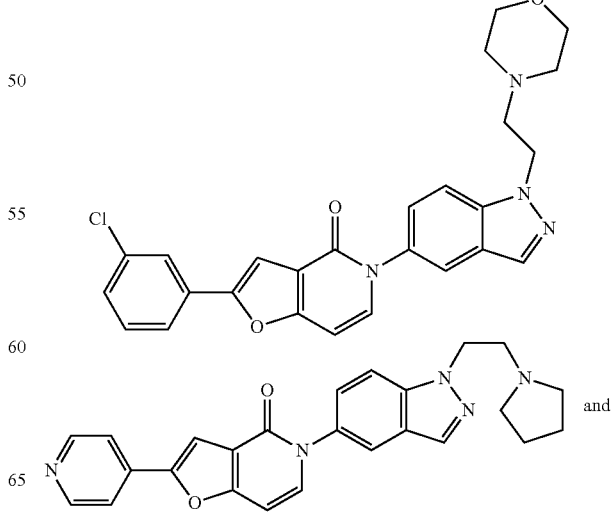

and

-continued

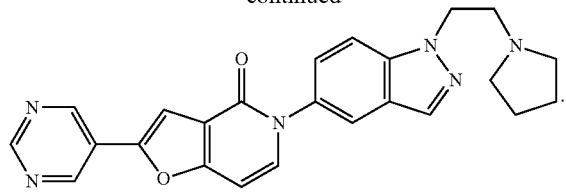

3) Bioorg. Med. Chem. Lett., 20(23), 7015-7019 (2010) (non-patent document 1) discloses a compound represented by the following formula:

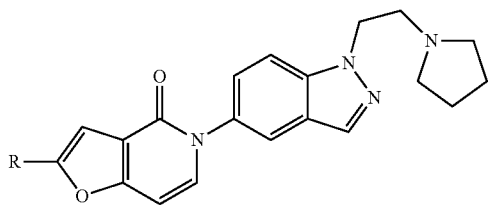

wherein R is phenyl, 4-fluorophenyl, 4-chlorophenyl, 2-chlorophenyl, 3-chlorophenyl, 2,4-dichlorophenyl, 4-chloro-2-fluorophenyl, 4-chloro-2-methoxyphenyl, pyridin-2-yl or pyrimidin-2-yl.

4) WO2011/130086 (patent document 3) and WO2011/127643 (patent document 4) disclose a compound represented by the formula:

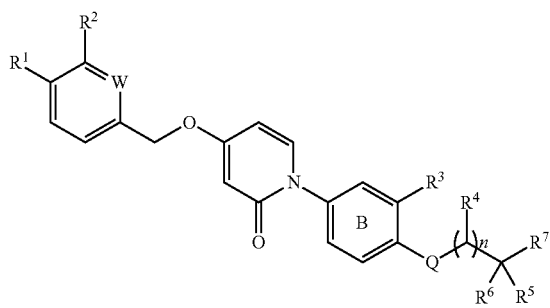

wherein
R$^1$ and R$^2$ are each independently selected from the group consisting of halogen, hydrogen, —OH, C$_1$-C$_6$ alkyl, —OC$_1$-C$_6$ alkyl, —O-halogen-substituted C$_1$-C$_6$ alkyl and halogen-substituted C$_1$-C$_6$ alkyl;
W is —N— or —CH—;
Q is —O—, —NH— or —C—, or forms heteroaryl together with R$^4$, aromatic ring B and R$^3$;
R$^3$ is halogen, hydrogen, —OC$_1$-C$_6$ alkyl, C$_1$-C$_5$ alkyl, —O-halogen substituted C$_1$-C$_5$ alkyl, halogen-substituted C$_1$-C$_5$ alkyl, cyano, SO$_2$C$_1$-C$_6$ alkyl or forms a heteroaryl ring together with aromatic ring B, Q and R$^4$;
R$^4$ is hydrogen, oxo, C$_1$-C$_6$ alkyl, halogen-substituted C$_1$-C$_5$ alkyl or forms heteroaryl together with aromatic ring B, R$^3$ and Q, or forms C$_3$-C$_5$ cycloalkyl together with R$^5$;
R$^5$, R$^6$ and R$^7$ are each independently selected from the group consisting of hydrogen, C$_1$-C$_6$ alkyl, halogen-substituted C$_1$-C$_6$ alkyl, C$_3$-C$_6$ cycloalkyl, halogen-substituted C$_3$-C$_6$ cycloalkyl, C$_1$-C$_6$ alkyl C$_3$-C$_6$ cycloalkyl, —OH, C$_1$-C$_6$ alkyl-OH and —OC$_1$-C$_6$ alkyl, or R$^5$ forms oxo group or C$_3$-C$_6$ cycloalkyl together with R$^6$, or R$^5$ forms C$_3$-C$_6$ cycloalkyl together with R$^4$, and at least one of R$^5$, R$^6$ and R$^7$ is not hydrogen, and
n is 1-3,
or a pharmaceutically acceptable salt thereof.

5) WO01/82925 (patent document 5) discloses a compound represented by the formula:

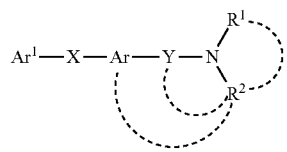

wherein
Ar$^1$ is a cyclic group optionally having substituent(s);
X and Y are the same or different and each is a spacer having a main chain of 1 to 6 atoms;
Ar is a fused polycyclic aromatic ring optionally having substituent(s);
R$^1$ and R$^2$ are the same or different and each is a hydrogen atom or a hydrocarbon group optionally having substituent(s), R$^1$ and R$^2$ optionally form, together with the adjacent nitrogen atom, a nitrogen-containing heterocycle optionally having substituent(s), R$^2$ optionally form, together with the adjacent nitrogen atom and Y, a nitrogen-containing heterocycle optionally having substituent(s), or R$^2$ optionally form, together with the adjacent nitrogen atom, Y and Ar, a nitrogen-containing fused ring optionally having substituent(s),
or a salt thereof.

6) WO2006/118320 (patent document 6) discloses a compound represented by the formula:

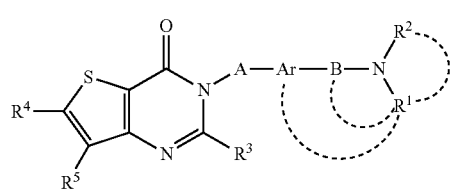

(I)

wherein
Ar is an optionally substituted ring;
A is a spacer having a main chain of 1 to 4 atoms;
B is a bond, a C$_{1-10}$ alkylene group or an oxygen atom;
R$^3$ and R$^5$ are each independently a hydrogen atom or a substituent;
R$^4$ is an optionally substituted cyclic group or an optionally substituted C$_{1-10}$ alkyl group;
R$^1$ and R$^2$ are each independently a hydrogen atom or a substituent, or R$^1$ is bonded to R$^2$ or B to form an optionally substituted nitrogen-containing heterocycle, or R$^1$ is bonded to Ar to form an optionally substituted nitrogen-containing fused heterocycle,
or a salt thereof.

DOCUMENT LIST

Patent Documents patent document 1: WO2007/029847
patent document 2: WO2008/086409
patent document 3: WO2011/130086 patent document 4: WO2011/127643
patent document 5: WO01/82925
patent document 6: WO2006/118320

Non-Patent Document non-patent document 1: Bioorg. Med. Chem. Lett., 20(23), 7015-7019 (2010)

SUMMARY OF THE INVENTION

Problems to be Solved by the Invention

The development of a compound having an MCH receptor antagonistic action and low toxicity, which is useful as an agent for the prophylaxis or treatment of obesity and the like is desired.

Means of Solving the Problems

The present inventors have conducted intensive studies of a compound having an MCH receptor antagonistic action and low toxicity [particularly, cardiotoxicity (e.g., human ether-a-go-go related gene (hERG) inhibitory activity), phospholipidosis (PLsis) inducing potential and the like, which sometimes pose problems in drug discovery], and found that compound (I) explained in the following has a superior MCH receptor antagonistic action and shows low toxicity such as cardiotoxicity (e.g., hERG inhibitory activity), PLsis inducing potential and the like as compared to conventional MCH receptor antagonists, which resulted in the completion of the present invention.

Accordingly, the present invention relates to

[1] a compound represented by the formula:

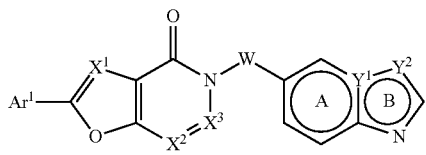

(I)

wherein
ring AB is optionally further substituted;
$Ar^1$ is an optionally substituted 5- or 6-membered aromatic ring group;
$X^1$ is $CR^1$ or N;
$X^2$ and $X^3$ are each independently CH or N;
one of $Y^1$ and $Y^2$ is a carbon atom and the other is a nitrogen atom;
W is a bond, an optionally substituted $C_{1-6}$ alkylene group, or an optionally substituted $C_{2-6}$ alkenylene group; and
$R^1$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group,
or a salt thereof (hereinafter sometimes to be abbreviated as "compound (I)");

[2] the compound of the aforementioned [1], wherein ring AB is optionally further substituted by 1 to 3 substituents selected from (1) a $C_{1-6}$ alkyl group, and
(2) a $C_{3-10}$ cycloalkyl group optionally substituted by a $C_{1-6}$ alkyl group optionally substituted by 1 to 3 hydroxy groups,
or a salt thereof;

[3] the compound of the aforementioned [1] or [2], wherein $Ar^1$ is a phenyl group, a pyridyl group, a thienyl group or a furyl group, each of which is optionally substituted by 1 to 3 halogen atoms, or a salt thereof;

[4] the compound of the aforementioned [1], [2] or [3], wherein $X^1$ is CH, or a salt thereof;

[5] the compound of the aforementioned [1], [2], [3] or [4], wherein $X^2$ and $X^3$ are each CH, or a salt thereof;

[6] the compound of the aforementioned [1], [2], [3], [4] or [5], wherein W is a bond, or a salt thereof;

[7] the compound of the aforementioned [1], wherein ring AB is further optionally substituted by 1 to 3 substituents selected from (1) a $C_{1-6}$ alkyl group and
(2) a $C_{3-10}$ cycloalkyl group optionally substituted by a $C_{1-6}$ alkyl group optionally substituted by 1 to 3 hydroxy groups;

$Ar^1$ is a phenyl group, a pyridyl group, a thienyl group or a furyl group, each of which is optionally substituted by 1 to 3 halogen atoms;
$X^1$ is $CR^1$;
$X^2$ and $X^3$ are each CH;
one of $Y^1$ and $Y^2$ is a carbon atom and the other is a nitrogen atom;
W is a bond; and
$R^1$ is a hydrogen atom, or a salt thereof;

[8] a medicament comprising the compound of the aforementioned [1], [2], [3], [4], [5], [6] or [7], or a salt thereof;

[9] the medicament of the aforementioned [8], which is a melanin-concentrating hormone receptor antagonist;

[10] the medicament of the aforementioned [8], which is an anorexigenic agent;

[11] the medicament of the aforementioned [8], which is a prophylactic or therapeutic agent for obesity;

[12] a method of antagonizing a melanin-concentrating hormone receptor in a mammal, comprising administering an effective amount of the compound of the aforementioned [1], [2], [3], [4], [5], [6] or [7] or a salt thereof to the mammal;

[13] a method of suppressing food intake in a mammal, comprising administering an effective amount of the compound of the aforementioned [1], [2], [3], [4], [5], [6] or [7] or a salt thereof to the mammal;

[14] a method for the prophylaxis or treatment of obesity in a mammal, comprising administering an effective amount of the compound of the aforementioned [1], [2], [3], [4], [5], [6] or [7] or a salt thereof to the mammal;

[15] use of the compound of the aforementioned [1], [2], [3], [4], [5], [6] or [7] or a salt thereof for the production of a melanin-concentrating hormone receptor antagonist;

[16] use of the compound of the aforementioned [1], [2], [3], [4], [5], [6] or [7] or a salt thereof for the production of an anorexigenic agent;

[17] use of the compound of the aforementioned [1], [2], [3], [4], [5], [6] or [7] or a salt thereof for the production of a prophylactic or therapeutic agent for obesity;

[18] the compound of the aforementioned [1], [2], [3], [4], [5], [6] or [7] or a salt thereof for use in antagonizing a melanin-concentrating hormone receptor;

[19] the compound of the aforementioned [1], [2], [3], [4], [5], [6] or [7] or a salt thereof for use in suppressing food intake;
[20] the compound of the aforementioned [1], [2], [3], [4], [5], [6] or [7] or a salt thereof for use in the prophylaxis or treatment of obesity; and the like.

Compound (I) has a high MCH receptor antagonistic action, and low toxicity such as cardiotoxicity (e.g., hERG inhibitory activity), PLsis inducing potential and the like, as compared to conventional MCH receptor antagonists. Therefore, compound (I) is highly useful as an agent for the prophylaxis or treatment of obesity and the like.

DETAILED DESCRIPTION OF THE INVENTION

The definitions of the symbols and terms used in the present invention are described in detail in the following.

In the present specification, the "halogen atom" means, unless otherwise specified, a fluorine atom, a chlorine atom, a bromine atom or an iodine atom.

In the present specification, the "$C_{1-6}$ alkyl group" means, unless otherwise specified, methyl, ethyl, propyl, isopropyl, n-butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 1,2,2-trimethylpropyl, 3,3-dimethylbutyl, 2-ethylbutyl and the like.

In the present specification, the "$C_{1-6}$ alkyl group" of the "optionally substituted $C_{1-6}$ alkyl group" optionally has 1 to 5 (preferably, 1 to 3) substituents at substitutable position(s). Examples of such substituent include the following substituent group A. When two or more substituents are present, the respective substituents may be the same or different.

Substituent Group A:
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group (e.g., methylcarbonyl, ethylcarbonyl) optionally substituted by 1 to 3 halogen atoms,
  (c) a $C_{1-6}$ alkoxy-carbonyl group (e.g., methoxycarbonyl, ethoxycarbonyl) optionally substituted by 1 to 3 halogen atoms,
  (d) a carbamoyl group optionally mono- or di-substituted by $C_{1-6}$ alkyl group(s) optionally substituted by 1 to 3 halogen atoms (e.g., methylcarbamoyl, ethylcarbamoyl), and
  (e) a formyl group;
(6) a $C_{1-6}$ alkyl-carbonyl group (e.g., methylcarbonyl, ethylcarbonyl) optionally substituted by 1 to 3 halogen atoms;
(7) a $C_{1-6}$ alkoxy-carbonyl group optionally substituted by 1 to 3 substituents selected from
  (a) a halogen atom, and
  (b) a $C_{1-6}$ alkoxy group;
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group,
  (e) an amino group optionally mono- or di-substituted by substituent(s) selected from a $C_{1-6}$ alkyl group and a $C_{1-6}$ alkoxy-carbonyl group,
  (f) a $C_{6-14}$ aryl group (e.g., phenyl),
  (g) a $C_{3-10}$ cycloalkyl group (e.g., cyclopropyl, cyclobutyl),
  (h) an aromatic heterocyclic group (e.g., thienyl, furyl), and
  (i) a hydroxy group;
(15) a $C_{2-6}$ alkenyloxy group (e.g., ethenyloxy) optionally substituted by 1 to 3 halogen atoms;
(16) a $C_{6-14}$ aryloxy group (e.g., phenyloxy, naphthyloxy);
(17) a $C_{1-6}$ alkyl-carbonyloxy group (e.g., acetyloxy, tert-butylcarbonyloxy);
(18) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(19) a nonaromatic heterocyclylcarbonyl group (e.g., pyrrolidinylcarbonyl, morpholinylcarbonyl, 1,1-dioxidothiomorpholinylcarbonyl) optionally substituted by 1 to 3 $C_{1-6}$ alkyl groups optionally substituted by 1 to 3 halogen atoms;
(20) a mercapto group;
(21) a $C_{1-6}$ alkylthio group (e.g., methylthio, ethylthio) optionally substituted by 1 to 3 halogen atoms;
(22) a $C_{7-13}$ aralkylthio group (e.g., benzylthio);
(23) a $C_{6-14}$ arylthio group (e.g., phenylthio, naphthylthio);

(24) a cyano group;
(25) a nitro group;
(26) a halogen atom;
(27) a $C_{1-3}$ alkylenedioxy group;
(28) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms; and
(29) a hydroxyimino group optionally substituted by a $C_{1-6}$ alkyl group optionally substituted by 1 to 3 $C_{6-14}$ aryl groups (e.g., phenyl).

In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.

In the present specification, the "$C_{1-6}$ alkoxy group" of the "optionally substituted $C_{1-6}$ alkoxy group" optionally has 1 to 5 (preferably, 1 to 3) substituents at substitutable position(s). Examples of such substituent include the above-mentioned substituent group A. When two or more substituents are present, the respective substituents may be the same or different.

In the present specification, the "$C_{3-10}$ cycloalkyl group" means, unless otherwise specified, cyclopropyl, cyclobutyl, cyclopentyl, cyclohexyl, cycloheptyl, cyclooctyl, adamantyl and the like.

In the present specification, the "$C_{3-10}$ cycloalkyl group" of the "optionally substituted $C_{3-10}$ cycloalkyl group" optionally has 1 to 5 (preferably, 1 to 3) substituents at substitutable position(s). Examples of such substituent include the following substituent group B. When two or more substituents are present, the respective substituents may be the same or different.

Substituent Group B:
(1) substituent group A;
(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a $C_{3-10}$ cycloalkyloxy group (preferably, cyclopropyloxy);
(3) a $C_{2-6}$ alkenyl group (e.g., ethenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a $C_{3-10}$ cycloalkyl group (e.g., cyclopropyl);
(4) a $C_{2-6}$ alkynyl group (e.g., ethynyl) optionally substituted by 1 to 3 $C_{3-10}$ cycloalkyl groups (e.g., cyclopropyl, cyclobutyl);
(5) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom; and
(6) an oxo group.

The "5- or 6-membered aromatic ring group" means a phenyl group or a 5- or 6-membered aromatic heterocyclic group.

In the present specification, examples of the "5- or 6-membered aromatic heterocyclic group" include a 5- or 6-membered aromatic heterocyclic group, containing, as a ring-constituting atom besides carbon atom, 1 to 4 hetero atoms selected from an oxygen atom, a sulfur atom and a nitrogen atom.

Preferable examples of the "5- or 6-membered aromatic heterocyclic group" include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,2,4-triazin-5-yl, 1,2,4-triazin-6-yl) and the like.

The "5- or 6-membered aromatic ring group" of the "optionally substituted 5- or 6-membered aromatic ring group" optionally has 1 to 5 (preferably, 1 to 3) substituents at substitutable position(s). Examples of such substituent include substituents selected from (1)-(5) of the above-mentioned substituent group B. When two or more substituents are present, the respective substituents may be the same or different.

The "$C_{1-6}$ alkylene group" means, unless otherwise specified, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$CH(CH_2CH_3)$—, —$CH(CH(CH_3)_2)$—$C(CH_3)_2$—, —$CH_2$—$CH(CH_3)$—, —$CH(CH_3)$—$CH_2$—, —$(CH(CH_3))_2$—, —$(CH_2)_2$—$C(CH_3)_2$—, —$(CH_2)_3$—$C(CH_3)_2$— and the like.

The "$C_{1-6}$ alkylene group" of the "optionally substituted $C_{1-6}$ alkylene group" optionally has 1 to 5 (preferably, 1 to 3) substituents at substitutable position(s). Examples of such substituent include the following substituent group C. When two or more substituents are present, the respective substituents may be the same or different.

Substituent Group C:
(1) substituent group A; and
(2) an oxo group.

The "$C_{2-6}$ alkenylene group" means, unless otherwise specified, —CH=CH—, —CH=CH—$CH_2$—, —$CH_2$—CH=CH—, —$C(CH_3)_2$—CH=CH—, —$CH_2$—CH=CH—$CH_2$—, —$CH_2$—$CH_2$—CH=CH—, —CH=CH—CH=CH—, —$C(CH_3)$=CH—, —CH=C($CH_3$)—, —CH=C($CH_2CH_3$)— and the like.

The "$C_{2-6}$ alkenylene group" of the "optionally substituted $C_{2-6}$ alkenylene group" optionally has 1 to 5 (preferably, 1 to 3) substituents at substitutable position(s). Examples of such substituent include the above-mentioned substituent group C. When two or more substituents are present, the respective substituents may be the same or different.

In the above-mentioned formula (I), preferable groups are as described below.

Ring AB may further have 1 to 5 (preferably, 1 to 3) substituents at substitutable position(s). Examples of such substituent include substituents selected from (1)-(5) of the above-mentioned substituent group B. When two or more substituents are present, the respective substituents may be the same or different.

Preferable examples of the substituent that Ring AB may further have include the following substituent group D and the like.

Ring AB may preferably have substituent(s) on ring B.
Substituent Group D:
(1) a halogen atom,
(2) a cyano group,
(3) a $C_{1-6}$ alkyl group optionally substituted by 1 to 3 substituents selected from a halogen atom, a cyano group, a hydroxy group, an optionally substituted $C_{1-6}$ alkoxy group, an optionally substituted $C_{3-10}$ cycloalkyl group, an optionally substituted aromatic ring group, —CO—$R^{7A}$ and —S(O)$_{n1}$—$R^{7B}$,
(4) a $C_{1-6}$ alkoxy group optionally substituted by 1 to 3 substituents selected from a halogen atom, a cyano group, a hydroxy group, an optionally substituted $C_{1-6}$ alkoxy group, an optionally substituted $C_{3-10}$ cycloalkyl group, an optionally substituted aromatic ring group, —CO—$R^{8A}$ and —S(O)$_{n2}$—$R^{8B}$,
(5) an optionally substituted $C_{2-6}$ alkenyl group,
(6) an optionally substituted cyclic group and
(7) —CO—$R^9$
wherein $R^{7A}$, $R^{7B}$, $R^{8A}$, $R^{8B}$ and $R^9$ are each independently an optionally substituted $C_{1-6}$ alkyl group, an optionally substituted $C_{3-10}$ cycloalkyl group or an optionally substituted amino group; and
n1 and n2 are each independently an integer of 0 to 2.

$R^{7A}$, $R^{7B}$, $R^{8A}$, $R^{8B}$ and $R^9$ are preferably each independently a $C_{1-6}$ alkyl group optionally substituted by 1 to 3 substituents selected from substituent group A,
a $C_{3-10}$ cycloalkyl group optionally substituted by 1 to 3 substituents selected from substituent group B, or
an amino group optionally substituted by 1 or 2 substituents selected from (1)-(5) of substituent group B.

$R^{7A}$, $R^{7B}$, $R^{8A}$, $R^{8B}$ and $R^9$ are more preferably each independently a $C_{1-6}$ alkyl group, a $C_{3-10}$ cycloalkyl group, a ($C_{1-6}$ alkyl)amino group, a di($C_{1-6}$ alkyl) amino group or a (hydroxy-$C_{1-6}$ alkyl)amino group.

Examples of the "cyclic group" of the "optionally substituted cyclic group" in substituent group D include a $C_{3-10}$ cycloalkyl group, a $C_{6-14}$ aryl group, a heterocyclic group and the like. Examples of the $C_{6-14}$ aryl group include phenyl, naphthyl, anthracenyl, phenanthrenyl, acenaphthylenyl and the like. Examples of the heterocyclic group include a 4- to 6-membered heterocyclic group containing, as a ring-constituting atom besides carbon atom, 1 to 4 hetero atoms selected from an oxygen atom, a sulfur atom and a nitrogen atom and the like.

The substituents that ring AB further optionally has are more preferably 1 to 3 substituents selected from
(1) a halogen atom,
(2) a cyano group,
(3) a $C_{1-6}$ alkyl group optionally substituted by 1 to 3 substituents selected from a halogen atom, a cyano group, a hydroxy group, a $C_{1-6}$ alkoxy group optionally substituted by 1 to 3 substituents selected from substituent group A, a $C_{3-10}$ cycloalkyl group optionally substituted by 1 to 3 substituents selected from substituent group B, an aromatic ring group optionally substituted by 1 to 3 substituents selected from (1)-(5) of substituent group B, —CO—$R^{7A}$ and —S(O)$_{n1}$—$R^{7B}$,
(4) a $C_{1-6}$ alkoxy group optionally substituted by 1 to 3 substituents selected from a halogen atom, a cyano group, a hydroxy group, a $C_{1-6}$ alkoxy group optionally substituted by 1 to 3 substituents selected from substituent group A, a $C_{3-10}$ cycloalkyl group optionally substituted by 1 to 3 substituents selected from substituent group B, an aromatic ring group optionally substituted by 1 to 3 substituents selected from (1)-(5) of substituent group B, —CO—$R^{8A}$ and —S(O)$_{n2}$—$R^{8B}$,
(5) a $C_{2-6}$ alkenyl group optionally substituted by 1 to 3 substituents selected from substituent group A,
(6) a $C_{3-10}$ cycloalkyl group optionally substituted by 1 to 3 substituents selected from substituent group B,
(7) a heterocyclic group (preferably a 4- to 6-membered heterocyclic group containing, as a ring-constituting atom besides carbon atom, 1 to 4 hetero atoms selected from an oxygen atom, a sulfur atom and a nitrogen atom, for example, tetrahydrofuranyl, dihydrooxazolyl, oxazolyl, isoxazolyl, pyrazolyl, oxadiazolyl, oxetanyl, thiazolyl) optionally substituted by 1 to 3 substituents selected from substituent group B, and
(8) —CO—$R^9$.

The substituents that ring AB further optionally has are further preferably 1 to 3 substituents selected from
(1) a cyano group,
(2) a $C_{1-6}$ alkyl group optionally substituted by 1 to 3 substituents selected from
  (a) a halogen atom (e.g., a fluorine atom, a chlorine atom),
  (b) a cyano group,
  (c) a hydroxy group,
  (d) a $C_{1-6}$ alkoxy group optionally substituted by 1 to 3 halogen atoms, and
  (e) a $C_{3-10}$ cycloalkyl group (e.g., cyclopropyl),
(3) a $C_{3-10}$ cycloalkyl group (e.g., cyclopropyl, cyclobutyl, cyclopentyl) optionally substituted by 1 to 3 substituents selected from
  (a) a halogen atom (e.g., a fluorine atom),
  (b) a cyano group,
  (c) a $C_{1-6}$ alkyl group optionally substituted by 1 to 3 substituents selected from a halogen atom and a hydroxy group,
  (d) a carbamoyl group,
  (e) a $C_{1-6}$ alkoxy group,
  (f) an oxo group,
  (g) a hydroxy group,
  (h) a $C_{1-6}$ alkoxy-carbonyl group, and
  (i) a carboxy group,
(4) a tetrahydrofuranyl group (e.g., tetrahydrofuran-2-yl, tetrahydrofuran-3-yl), a dihydrooxazolyl group (e.g., 4,5-dihydro-1,3-oxazol-2-yl), an oxazolyl group (e.g., 1,3-oxazol-5-yl, 1,3-oxazol-4-yl), an isoxazolyl group (e.g., 1,2-oxazol-5-yl, 1,2-oxazol-3-yl), a pyrazolyl group (e.g., 1H-pyrazol-3-yl), an oxadiazolyl group (e.g., 1,3,4-oxadiazol-2-yl), an oxetanyl group (e.g., oxetan-3-yl) or a thiazolyl group (e.g., thiazol-5-yl), each of which is optionally substituted by 1 to 3 substituents selected from a $C_{1-6}$ alkyl group and a $C_{3-10}$ cycloalkyl group, and
(5) —CO—$R^{9A}$
wherein $R^{9A}$ is a $C_{1-6}$ alkyl group, a $C_{3-10}$ cycloalkyl group (e.g., cyclopropyl), a ($C_{1-6}$ alkyl)amino group, a di($C_{1-6}$ alkyl)amino group or a (hydroxy-$C_{1-6}$ alkyl)amino group.

The substituents that ring AB optionally has are furthermore preferably 1 to 3 substituents selected from
(1) a $C_{1-6}$ alkyl group optionally substituted by 1 to 3 substituents selected from
  (a) a halogen atom (e.g., a fluorine atom, a chlorine atom),
  (b) a cyano group, (c) a hydroxy group,
(d) a $C_{1-6}$ alkoxy group optionally substituted by 1 to 3 halogen atoms, and
(e) a $C_{3-10}$ cycloalkyl group (e.g., cyclopropyl), and
(2) a $C_{3-10}$ cycloalkyl group (e.g., cyclopropyl, cyclobutyl, cyclopentyl) optionally substituted by 1 to 3 substituents selected from
(a) a halogen atom (e.g., a fluorine atom),
(b) a cyano group,
(c) a $C_{1-6}$ alkyl group optionally substituted by 1 to 3 substituents selected from a halogen atom and a hydroxy group,
(d) a carbamoyl group,
(e) a $C_{1-6}$ alkoxy group,
(f) an oxo group,
(g) a hydroxy group,
(h) a $C_{1-6}$ alkoxy-carbonyl group, and
(i) a carboxy group.

The substituents that ring AB further optionally has are particularly preferably 1 to 3 (preferably 1 or 2) substituents selected from
(1) a $C_{1-6}$ alkyl group, and
(2) a $C_{3-10}$ cycloalkyl group (e.g., cyclopropyl) optionally substituted by a $C_{1-6}$ alkyl group optionally substituted by 1 to 3 hydroxy groups.

$Ar^1$ is an optionally substituted 5- or 6-membered aromatic ring group.

Examples of $Ar^1$ include an optionally substituted phenyl group or an optionally substituted 5- or 6-membered aromatic heterocyclic group (preferably, a 5- or 6-membered aromatic heterocyclic group containing, besides carbon atom, 1 to 4 hetero atoms selected from an oxygen atom, a sulfur atom and a nitrogen atom).

$Ar^1$ is preferably
a phenyl group optionally substituted by 1 to 3 substituents selected from (1)-(5) of substituent group B, or a 5- or 6-membered aromatic heterocyclic group (preferably, a 5- or 6-membered aromatic heterocyclic group containing, besides carbon atom, 1 to 4 hetero atoms selected from an oxygen atom, a sulfur atom and a nitrogen atom, for example, pyridyl, thienyl, thiazolyl, pyrazolyl, pyrimidinyl, furyl) optionally substituted by 1 to 3 substituents selected from (1)-(5) of substituent group B.

$Ar^1$ is more preferably a phenyl group, a pyridyl group (e.g., pyridin-2-yl, pyridin-3-yl, pyridin-4-yl), a thienyl group (e.g., thiophen-2-yl, thiophen-3-yl), a thiazolyl group (e.g., thiazol-2-yl, thiazol-5-yl), a pyrazolyl group (e.g., pyrazol-3-yl), a pyrimidinyl group (e.g., pyrimidin-5-yl) or a furyl group (e.g., furan-2-yl), each of which is optionally substituted by 1 to 3 substituents selected from
(a) a halogen atom (e.g., a fluorine atom, a chlorine atom),
(b) a cyano group,
(c) a $C_{1-6}$ alkyl group optionally substituted by 1 to 3 halogen atoms (e.g., trifluoromethyl group), and
(d) a $C_{1-6}$ alkoxy group optionally substituted by 1 to 3 halogen atoms.

$Ar^1$ is more preferably a phenyl group, a pyridyl group (e.g., pyridin-2-yl, pyridin-3-yl, pyridin-4-yl), a thienyl group (e.g., thiophen-2-yl, thiophen-3-yl) or a furyl group (e.g., furan-2-yl), each of which is optionally substituted by 1 to 3 substituents selected from
(a) a halogen atom (e.g., a fluorine atom, a chlorine atom),
(b) a cyano group,
(c) a $C_{1-6}$ alkyl group optionally substituted by 1 to 3 halogen atoms (e.g., trifluoromethyl group), and
(d) a $C_{1-6}$ alkoxy group optionally substituted by 1 to 3 halogen atoms.

$Ar^1$ is furthermore preferably a phenyl group, a pyridyl group (e.g., pyridin-2-yl, pyridin-3-yl, pyridin-4-yl), a thienyl group (e.g., thiophen-2-yl, thiophen-3-yl) or a furyl group (e.g., furan-2-yl), each of which is optionally substituted by 1 to 3 halogen atoms (e.g., a fluorine atom, a chlorine atom).

Particularly preferable examples of $Ar^1$ include a phenyl group and a pyridyl group, each of which is optionally substituted by 1 to 3 halogen atoms (e.g., a fluorine atom, a chlorine atom).

$X^1$ is $CR^1$ or N.
$X^1$ is preferably $CR^1$.
$R^1$ is a hydrogen atom, a halogen atom, an optionally substituted $C_{1-6}$ alkyl group, an optionally substituted $C_{3-10}$ cycloalkyl group, or an optionally substituted $C_{1-6}$ alkoxy group.

$R^1$ is preferably
a hydrogen atom,
a halogen atom,
a $C_{1-6}$ alkyl group optionally substituted by 1 to 3 substituents selected from substituent group A,
a $C_{3-10}$ cycloalkyl group optionally substituted by 1 to 3 substituents selected from substituent group B, or
a $C_{1-6}$ alkoxy group optionally substituted by 1 to 3 substituents selected from substituent group A.

$R^1$ is more preferably
a hydrogen atom, or
a $C_{1-6}$ alkyl group optionally substituted by 1 to 3 substituents selected from a halogen atom, a hydroxy group and a $C_{1-6}$ alkoxy group.

$R^1$ is more preferably a hydrogen atom or a $C_{1-6}$ alkyl group, particularly preferably a hydrogen atom.

$X^1$ is preferably CH.
$X^2$ and $X^3$ are each independently CH or N.
A preferable combination of $X^2$ and $X^3$ is
$X^2$ and $X^3$ each being CH, or
$X^2$ being N and $X^3$ being CH, or
$X^2$ being CH and $X^3$ being N.
$X^2$ and $X^3$ are each preferably CH.

A group represented by the formula

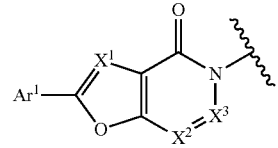

is preferably

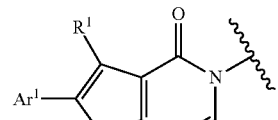

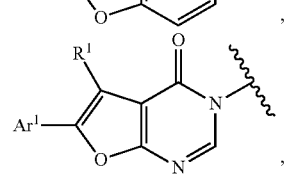

,

-continued

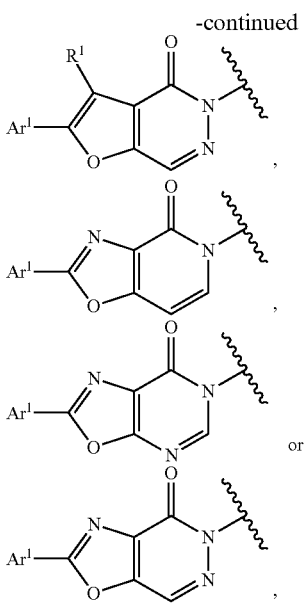

more preferably

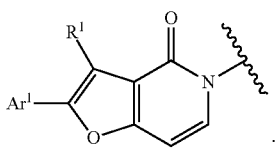

One of $Y^1$ and $Y^2$ is a carbon atom and the other is a nitrogen atom.

A group represented by the formula

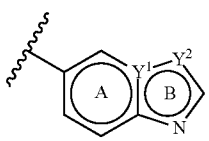

is

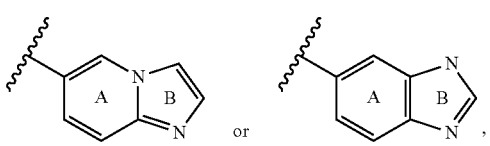

and ring AB is further optionally substituted.

In the present specification, a ring represented by the formula

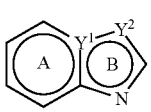

is referred to as ring AB.

W is a bond, an optionally substituted $C_{1-6}$ alkylene group, or an optionally substituted $C_{2-6}$ alkenylene group.

W is preferably
a bond,
a $C_{1-6}$ alkylene group optionally substituted by 1 to 3 substituents selected from substituent group C, or
a $C_{2-6}$ alkenylene group optionally substituted by 1 to 3 substituents selected from substituent group C.

W is more preferably
a bond,
a $C_{1-6}$ alkylene group optionally substituted by 1 to 3 substituents selected from an oxo group and a hydroxy group, or
a $C_{2-6}$ alkenylene group optionally substituted by 1 to 3 substituents selected from an oxo group and a hydroxy group.

W is more preferably a bond, a $C_{1-6}$ alkylene group or a $C_{2-6}$ alkenylene group.

W is particularly preferably a bond.

Preferable examples of compound (I) include the following compounds.

[Compound (I-A)]

Compound (I) wherein
ring AB is further optionally substituted by 1 to 3 substituents selected from
(1) a $C_{1-6}$ alkyl group, and
(2) a $C_{3-10}$ cycloalkyl group (e.g., cyclopropyl) optionally substituted by a $C_{1-6}$ alkyl group optionally substituted by 1 to 3 hydroxy groups;
$Ar^1$ is a phenyl group, a pyridyl group (e.g., pyridin-2-yl, pyridin-3-yl, pyridin-4-yl), a thienyl group (e.g., thiophen-2-yl, thiophen-3-yl) or a furyl group (e.g., furan-2-yl), each of which is optionally substituted by 1 to 3 halogen atoms (e.g., a fluorine atom, a chlorine atom);
$X^1$ is $CR^1$;
$X^2$ and $X^3$ are each CH;
one of $Y^1$ and $Y^2$ is a carbon atom and the other is a nitrogen atom;
W is a bond; and
$R^1$ is a hydrogen atom, or a salt thereof.

[Compound (I-B)]

Compound (I) wherein
ring AB is further optionally substituted by 1 to 3 substituents selected from
(1) a $C_{1-6}$ alkyl group, and
(2) a $C_{3-10}$ cycloalkyl group (e.g., cyclopropyl) optionally substituted by a $C_{1-6}$ alkyl group optionally substituted by 1 to 3 hydroxy groups;
$Ar^1$ is a phenyl group or a pyridyl group (e.g., pyridin-2-yl, pyridin-3-yl, pyridin-4-yl), each of which is optionally substituted by 1 to 3 halogen atoms (e.g., a fluorine atom, a chlorine atom);
$X^1$ is $CR^1$;
$X^2$ and $X^3$ are each CH;
one of $Y^1$ and $Y^2$ is a carbon atom and the other is a nitrogen atom;
W is a bond; and
$R^1$ is a hydrogen atom, or a salt thereof.

More preferable examples of compound (I) include those described in the following Examples and salts thereof.

[Compound (I-C)]

2-(4-chlorophenyl)-5-(2-cyclopropyl-3-methylimidazo[1,2-a]pyridin-6-yl)furo[3,2-c]pyridin-4(5H)-one 2-(4-chlorophenyl)-5-(2-cyclopropyl-1-methyl-1H-benzimidazol-6-yl)furo[3,2-c]pyridin-4(5H)-one 2-(5-chloropyridin-2-yl)-5-(2-cyclopropyl-3-methylimidazo[1,2-a]pyridin-6-yl)furo[3,2-c]pyridin-4(5H)-one 2-(4-chlorophenyl)-5-(2-((1RS,2SR)-2-(2-hydroxypropan-2-yl)cyclopropyl)-1-methyl-1H-benzimidazol-6-yl)furo[3,2-c]pyridin-4(5H)-one When compound (I) is in the form of a salt, concrete examples thereof include pharmaceutically acceptable salts, for example, salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N'-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be any of an anhydrate or a hydrate.

In addition, compound (I) may be any of non-solvate and solvate.

Moreover, compound (I) may be labeled with an isotope (e.g., $^3H$, $^{11}C$, $^{14}C$, $^{18}F$, $^{35}S$, $^{125}I$).

Furthermore, compound (I) may also be a deuterium exchange compound wherein $^1H$ is converted to $^2H(D)$.

Compound (I) labeled with or substituted by an isotope can be used, for example, as a tracer used for Positron Emission Tomography (PET) (PET tracer), and is useful in the field of medical diagnosis and the like.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [α-methoxy-α-(trifluoromethyl)phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

Compound (I) may also be a prodrug, and a prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);

a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl- 2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

The production methods of compound (I) are explained in the following.

Compound (I) can be produced by, for example, a method shown below or a method analogous thereto, though not limited thereto.

In each of the following schemes, each starting compound may form a salt as long as it does not inhibit the reaction and, as the salt, those exemplified as the salt of the compound represented by the aforementioned formula (I) is used.

In each of the following schemes, as the starting compound, unless specific production method is stated, a commercially available one is easily available, or can be produced by a method known per se or a method analogous thereto.

A solvent to be used for the reaction of each of the following schemes is not particularly limited as long as it does not inhibit the reaction and dissolves the starting material to some extent. Examples thereof include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, 1,2-dimethoxyethane and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; water and the like. These solvents may be mixed and used at an appropriate ratio. The reaction temperature is not higher than the boiling points of the aforementioned solvents, and is generally −100° C. to 250° C. In some cases, pressure-resistant reaction conditions and the like may be employed, and the reaction may be performed at a temperature not lower than the boiling point of the solvent. The reaction time is generally 0.5 hr to 100 hr.

In each of the following reactions, the "room temperature" means 15° C. to 30° C.

Compound (Ia) which is compound (I) wherein W is a bond can be produced by reacting compound (2) with compound (3a) shown in the following production method 1-1.

[Production Method 1-1]

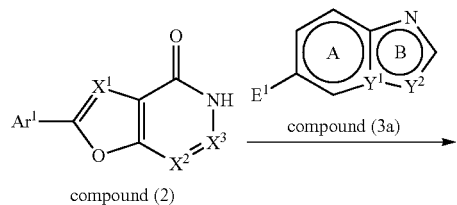

compound (2)

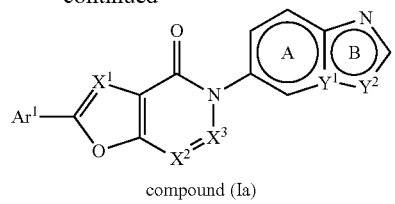

-continued compound (Ia)

wherein $E^1$ is a leaving group (e.g., halogen atom such as chlorine, bromine, iodine and the like, substituted sulfonic acid ester such as methanesulfonic acid ester, p-toluenesulfonic acid ester and the like, boronic acid etc.), and other symbols are each as defined above.

In production method 1-1, compound (Ia) is obtained using about 1.0 to 10.0 mol, preferably about 1.0 to 5.0 mol, of compound (3a), about 1.0 to 10.0 mol, preferably about 1.0 to 5.0 mol, of a base, and about 0.000001 to 5 mol, preferably about 0.0001 to 2 mol, of a metal catalyst, per 1 mol of compound (2).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo [5.4.0]undec-7-ene and the like; and the like. Two or more kinds of these bases may be mixed and used at an appropriate ratio.

Examples of the metal catalyst include copper and a salt thereof (e.g., copper(II) acetate, copper(II) iodide and the like), palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper and a salt thereof are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally room temperature to 250° C., preferably 50° C. to 200° C.

In addition, this reaction may be performed using a ligand. As the ligand, organic amine compounds such as N,N'-dimethylethylenediamine, N,N'-dimethylcyclohexane-1,2-diamine, 2,2'-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned.

The amount of the ligand to be used is generally about 1.0 to 10.0 mol, preferably about 1.0 to 5.0 mol, relative to the metal catalyst per mol.

The obtained compound (Ia) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2) can be produced according to the method described in the following production method or a method analogous thereto, or a method known per se.

Compound (3a) can be produced according to the method described in the following production method or a method analogous thereto, or a method known per se.

Compound (Ib) which is compound (I) wherein W is an optionally substituted $C_{1-6}$ alkylene group or an optionally substituted $C_{2-6}$ alkenylene group can be produced by reacting compound (2) with compound (3b) shown in the following production method 1-2.

[Production Method 1-2]

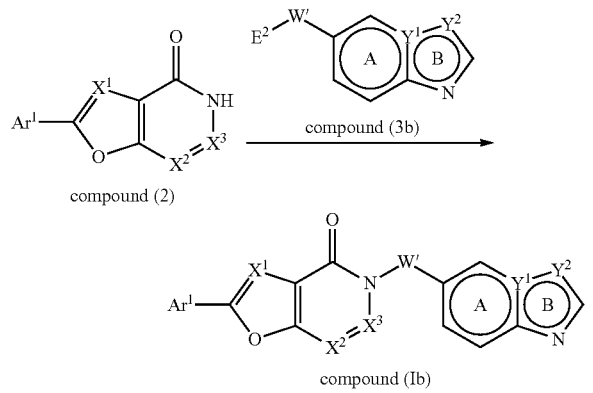

compound (2)

compound (Ib)

wherein $E^2$ is a leaving group (e.g., halogen atom such as chlorine, bromine, iodine and the like, substituted sulfonic acid ester such as methanesulfonic acid ester, p-toluenesulfonic acid ester etc., and the like), W' is an optionally substituted $C_{1-6}$ alkylene group or an optionally substituted $C_{2-6}$ alkenylene group, and other symbols are each as defined above.

In production method 1-2, compound (Ib) is obtained by using about 1.0 to 10.0 mol, preferably about 1.0 to 5.0 mol, of compound (3b), and about 1.0 to 10.0 mol, preferably about 1.0 to 5.0 mol, of a base, per 1 mol of compound (2).

Examples of the base include inorganic salts such as potassium hydride, sodium hydride, potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is room temperature to 250° C., preferably 50° C. to 200° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compound (Ib) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2) can be produced according to the method described in the following production method or a method analogous thereto, or a method known per se.

Compound (3b) can be produced according to the method described in the following production method or a method analogous thereto, or a method known per se.

Compound (2) which is a starting compound in production method 1-1 and production method 1-2 can be produced, for example, from compound (4) via compound (5) shown in the following production method 2-1.

[Production Method 2-1]

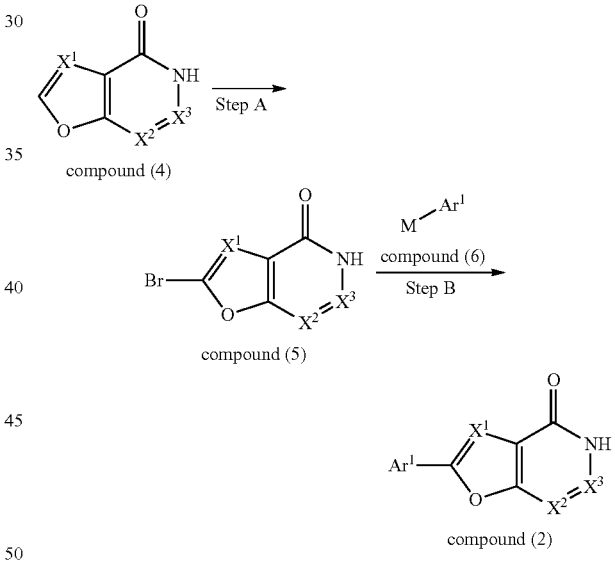

compound (4)

compound (5)

compound (2)

wherein M is a metal (e.g., boric acid, borate, alkyltin, zinc, magnesium halide etc.), and other symbols are each as defined above.

<Step A>

In step A, compound (5) is obtained by brominating compound (4) with 1.0 to 5.0 mol, preferably 1.0 to 2.0 mol, of a brominating reagent per 1 mol of compound (4).

Examples of the brominating reagent include bromine, hydrogen bromide, N-bromosuccinimide and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; organic acids such as acetic acid, and the like, and the like. Two or more kinds of these solvents may be mixed and used at an appropriate ratio.

The reaction time is generally 1 to 60 hr, preferably 1 to 24 hr. The reaction temperature is generally −50° C. to 150° C., preferably 0° C. to 100° C.

The obtained compound (5) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (4), a commercially available reagent can be used, or it can be produced according to the method described in the following production method or a method analogous thereto, or a method known per se.

<Step B>

In step B, compound (2) is obtained by using about 1.0 to 10.0 mol, preferably about 1.0 to 5.0 mol, of compound (6), about 1.0 to 10.0 mol, preferably about 1.0 to 5.0 mol, of a base, and about 0.000001 to 5 mol, preferably about 0.0001 to 2 mol, of a metal catalyst, per 1 mol of compound (5).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene, and the like, and the like. Two or more kinds of these bases may be mixed and used at an appropriate ratio.

Examples of the metal catalyst include copper and a salt thereof (e.g., copper(II) acetate, copper(II) iodide and the like), palladium compound (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compound (e.g., tetrakis(triphenylphosphine)nickel and the like), rhodium compound (e.g., tris(triphenylphosphine)rhodium chloride and the like), platinum compound and the like. Among these, a palladium compound is preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, 1,2-dimethoxyethane and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio. Furthermore, water may be mixed at an appropriate ratio.

When a metal catalyst unstable to oxygen is used for this reaction, the reaction is preferably performed under an inactive gas (e.g., argon, nitrogen and the like) atmosphere.

The reaction time is generally 15 min to 60 hr, preferably 30 min to 24 hr. The reaction temperature is room temperature to 250° C., preferably 50° C. to 200° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

In addition, this reaction may be performed by adding a ligand. Examples of the ligand include organic amine compounds such as N,N'-dimethylethylenediamine, N,N'-dimethylcyclohexane-1,2-diamine, 2,2-bipyridyl and the like; organic phosphorous compounds such as triphenylphosphine, tri-tert-butylphosphine, tricyclohexylphosphine, BINAP (2,2'-bis(diphenylphosphino)-1,1'-binaphthyl) and the like. The amount of the ligand to be used is generally about 1.0 to 10.0 mol, preferably about 1.0 to 5.0 mol, per 1 mol of the metal catalyst.

The obtained compound (2) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (6), a commercially available reagent can be used, or it can be produced according to a method known per se.

Compound (2a) which is compound (2) wherein $X^2$ and $X^3$ are each CH, which is a starting compound in production method 1-1 and production method 1-2, and compound (5a) which is compound (5) wherein $X^2$ and $X^3$ are each CH, which is an intermediate compound in production method 2-1, can be produced, as another method, for example, from compound (7) shown in the following production method 2-2. Furthermore, compound (4a) which is compound (4) wherein $X^2$ and $X^3$ are each CH, which is a starting compound in production method 2-1, can also be produced in the same manner.

[Production Method 2-2]

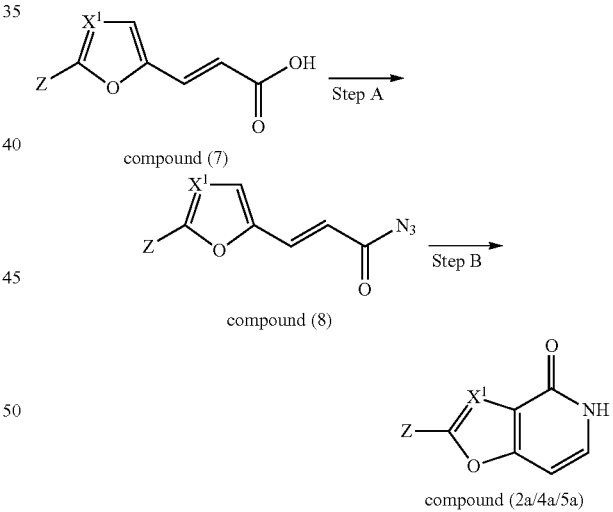

compound (2a/4a/5a)

wherein Z is $Ar^1$, a bromine atom or a hydrogen atom, and other symbols are each as defined above.

<Step A>

In step A, compound (8) is obtained by reacting compound (7) with about 1.0 to 100 mol, preferably about 1.0 to 10 mol, of formic acid ester, in the presence of about 1.0 to 100 mol, preferably about 1.0 to 10 mol, of a base per 1 mol of compound (7), and using about 1.0 to 20 mol, preferably about 1.0 to 5 mol, of sodium azide.

Examples of the formic acid ester include methyl chloroformate, ethyl chloroformate, isopropyl chloroformate and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably 0° C. to 100° C.

The obtained compound (8) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (7), a commercially available reagent can be used, or it can be produced by a method known per se.
<Step B>

In step B, compound (2a/4a/5a) is obtained by cyclizing 1 mol of compound (8) in the presence of about 1.0 to 100 mol, preferably about 1.0 to 10 mol, of an organic amine compound.

Examples of the organic amine compound include tributylamine, triethylamine and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is room temperature to 250° C., preferably 150° C. to 250° C.

The obtained compounds (2a/4a/5a) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2b) which is compound (2) wherein $X^1$ is $CR^1$, $X^2$ is N, and $X^3$ is CH, which is a starting compound in production method 1-1 and production method 1-2, can be produced, as another method, for example, from compound (9) shown in the following production method 2-3. Furthermore, compound (4b) which is compound (4) wherein $X_1$ is $CR^1$, $X^2$ is N, and $X^3$ is CH, which is a starting compound in production method 2-1, can also be produced in the same manner.

[Production Method 2-3]

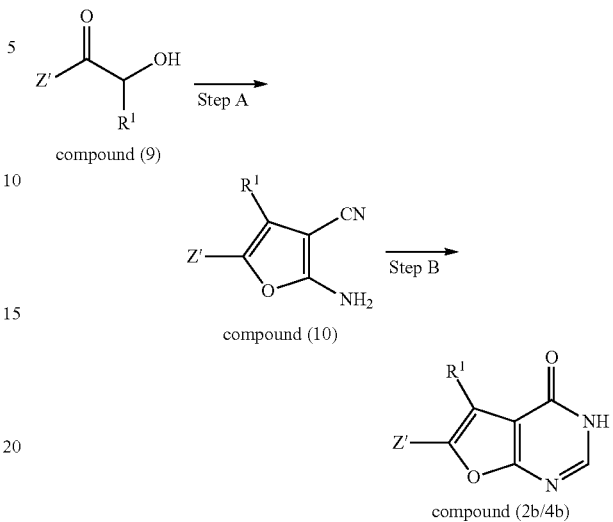

wherein Z' is $Ar^1$ or a hydrogen atom, and other symbols are each as defined above.
<Step A>

Step A is performed by a method known per se, for example, the method described in US2009/0318475 and the like, or a method analogous thereto. That is, compound (10) is obtained by cyclizing 1 mol of compound (9) by using about 1.0 to 100 mol, preferably about 1.0 to 10 mol, of malononitrile and about 1.0 to 100 mol, preferably about 1.0 to 10 mol, of a base.

Examples of the base include amines such as methylamine, ethylamine, diisopropylamine, triethylamine, N,N-dimethylaniline, 1,8-diazabicyclo[5.4.0]undec-7-ene, and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 1 hr to 24 hr. The reaction temperature is 0° C. to 250° C., preferably room temperature to 250° C.

The obtained compound (10) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (9), a commercially available reagent can be used, or it can be produced by a method known per se.
<Step B>

Step B is performed by a method known per se, for example, the method described in US2009/0318475 and the like, or a method analogous thereto. That is, compound (2b/4b) is obtained by cyclizing 1 mol of compound (10)

with about 1.0 to 100 mol, preferably about 1.0 to 10 mol, of formic acid, and about 1.0 to 100 mol, preferably about 1.0 to 10 mol, of acid anhydride.

Examples of acid anhydride include acetic anhydride, trifluoroacetic anhydride and the like. In addition, these acid anhydrides may be used as solvents.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, diphenyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 1 hr to 24 hr. The reaction temperature is 0° C. to 250° C., preferably room temperature to 250° C.

The obtained compounds (2b/4b) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2c) which is compound (2) wherein $X^2$ is CH and $X^3$ is N, which is a starting compound in production method 1-1 and production method 1-2, can be produced, as another method, for example, from compound (11) shown in the following production method 2-4. Furthermore, compound (4c) which is compound (4) wherein $X^2$ is CH and $X^3$ is N, which is a starting compound in production method 2-1, can also be produced in the same manner.

[Production Method 2-4]

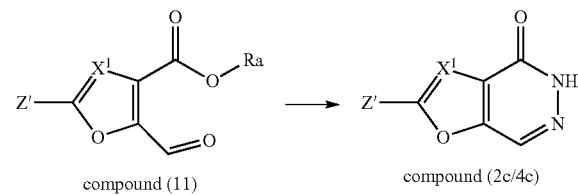

compound (11)    compound (2c/4c)

wherein Ra is a $C_{1-6}$ alkyl group, Z' is $Ar^1$ or a hydrogen atom, and other symbols are each as defined above.

In production method 2-4, compound (2c/4c) is obtained by reacting compound (11) with about 1.0 to 10.0 mol, preferably about 1.0 to 5.0 mol, of hydrazine or a hydrate thereof in the presence of an acid. The amount of the acid to be used is about 0.01 to 100 mol, preferably about 0.1 to 50 mol, relative to compound (11).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide, and the like, and the like. In addition, these acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 15 min to 24 hr. The reaction temperature is 0° C. to 250° C., preferably room temperature to 250° C. This reaction may be performed in a microwave reactor. In this case, the reaction time is generally 5 min to 24 hr, preferably 30 min to 2 hr. The reaction temperature is generally room temperature to 250° C., preferably 50° C. to 200° C.

The obtained compounds (2c/4c) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (11), a commercially available reagent can be used, or it can be produced by a method known per se.

Compound (3a') which is compound (3a) wherein $Y^1$ is a nitrogen atom and $Y^2$ is a carbon atom, which is a starting compound in production method 1-1, and compound (3b') which is compound (3b) wherein $Y^1$ is a nitrogen atom and $Y^2$ is a carbon atom, which is a starting compound in production method 1-2 can be produced by reacting compound (12) with compound (13), or alkylation of compound (14), followed by a cyclization reaction.

[Production Method 3-1]

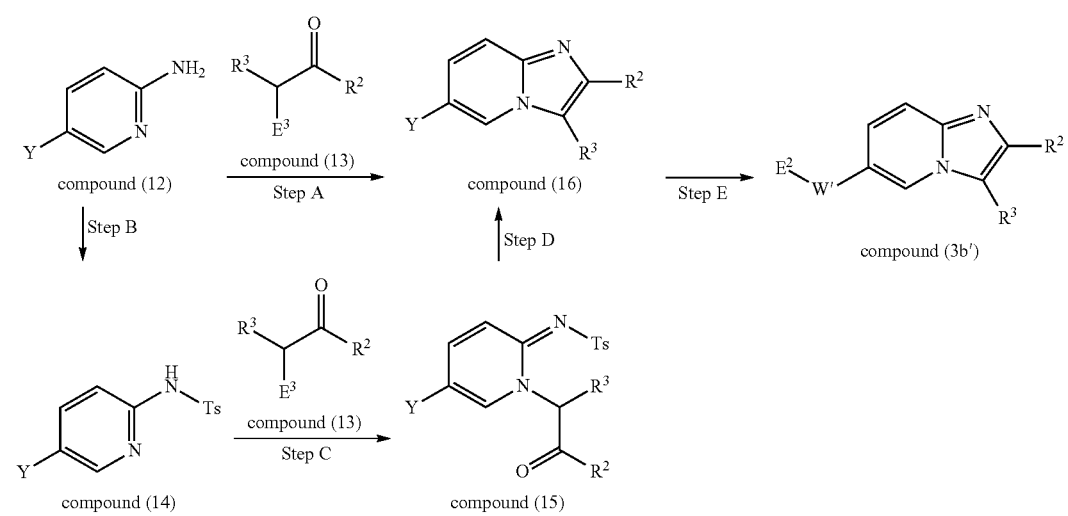

wherein Y is $E^1$ or HO—W'— wherein the hydroxy group optionally has a protecting group, $E^3$ is a halogen atom (e.g., halogen atom such as chlorine, bromine, iodine and the like), $R^2$ and $R^3$ are each a substituent, Ts is a p-toluenesulfonyl group, and other symbols are each as defined above. Examples of the substituent for $R^2$ or $R^3$ include those exemplified as the substituents that ring AB optionally further has.

<Step A>

In step A, compound (16) is obtained by reacting about 1.0 to 10.0 mol, preferably 1.0 to 5.0 mol, of compound (13) per 1 mol of compound (12). When Y is $E^1$, compound (16) is is compound (3a').

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 30 min to 48 hr, preferably 1 hr to 24 hr. The reaction temperature is generally room temperature to 200° C., preferably 80° C. to 150° C.

The obtained compound (16) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (12), a commercially available reagent can be used, or it can be produced by a method known per se.

As compound (13), a commercially available reagent can be used, or it can be produced by a method known per se.

<Step B>

In step B, compound (14) is obtained by reacting about 0.9 to 1.5 mol, preferably 1 to 1.2 mol, of p-toluenesulfonyl chloride in the presence of about 1.0 to 10 mol, preferably about 1.0 to 5.0 mol, of a base per 1 mol of compound (12).

Examples of the base include pyridine, triethylamine and the like.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; organic bases such as pyridine, triethylamine and the like, and the like. Two or more kinds of these solvents may be mixed and used at an appropriate ratio. Furthermore, the above-mentioned base may be used as a solvent.

The reaction time is generally 1 hr to 48 hr, preferably 1 hr to 24 hr. The reaction temperature is generally 0° C. to 150° C., preferably 0° C. to 80° C.

The obtained compound (14) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In step C, compound (15) is obtained by a reaction according to the method of production method 3-1, step A, or a method analogous thereto.

<Step D>

In step D, compound (16) is obtained by reacting about 1 to 10 mol, preferably about 1 to 5 mol, of acid anhydride per 1 mol of compound (15). When Y is $E^1$, compound (16) is compound (3a').

Examples of the acid anhydride include acetic anhydride, trifluoroacetic anhydride and the like. In addition, these acids may be used as solvents.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane, and the like, and the like. Two or more kinds of these solvents may be mixed and used at an appropriate ratio.

The reaction time is generally 1 hr to 48 hr, preferably 1 hr to 24 hr. The reaction temperature is generally room temperature to 120° C., preferably room temperature to 100° C.

The obtained compound (16) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step E>

In step E, the object compound (3b') is obtained by deprotection of compound (16) wherein Y is HO—W'—, wherein the hydroxy group optionally has a protecting group, as necessary, and subjecting compound (16) to a halogenation or sulfonylation reaction known per se.

Compound (3a") which is compound (3a) wherein $Y^1$ is a carbon atom and $Y^2$ is a nitrogen atom, which is a starting compound in production method 1-1, and compound (3b") which is compound (3b) wherein $Y^1$ is a carbon atom and $Y^2$ is a nitrogen atom, which is a starting compound in production method 1-2, can be produced from compound (17) via compound (18) and compound (20) or from compound (17) via compound (22) and compound (23), according to the following production method 3-2.

[Production Method 3-2]

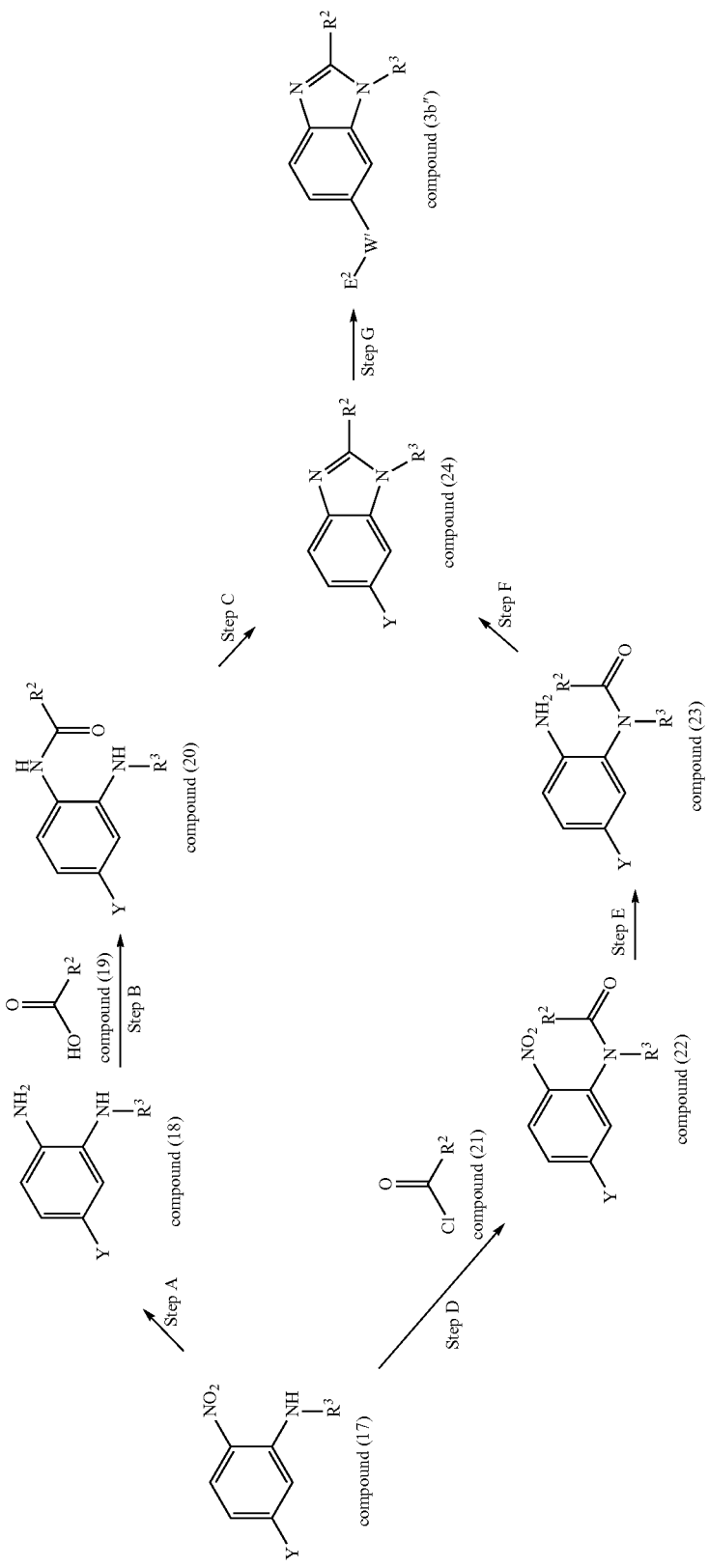

wherein each symbol is as defined above.

<Step A>

In step A, compound (18) is produced by reduction using about 0.01 to 5.0 mol, preferably about 0.01 to 2.0 mol, of a metal catalyst per 1 mol of compound (17) under a hydrogen atmosphere.

Examples of the metal catalyst include palladium-carbon, palladium hydroxide-carbon, platinum oxide, platinum and the like.

This reaction is preferably performed using a solvent inert to the reaction. The solvent is not particularly limited as long as the reaction proceeds. Preferable examples thereof include alcohols such as methanol, ethanol, propanol and the like; aromatic hydrocarbons such as benzene, toluene and the like; saturated hydrocarbons such as cyclohexane, hexane and the like; ethers such as tetrahydrofuran, 1,4-dioxane, 1,2-dimethoxyethane and the like; amides such as N,N-dimethylformamide, N,N-dimethylacetamide and the like; sulfoxides such as dimethyl sulfoxide and the like; solvents such as water and the like or a mixed solvent thereof and the like.

The reaction time is generally 1 hr to 60 hr, preferably 5 hr to 48 hr. The reaction temperature is generally –50° C. to 150° C., preferably 0 to 100° C. The pressure is about 1 to 10 atm, preferably about 1 to 5 atm.

The obtained compound (18) can be used directly as a reaction mixture, or as a crude product, for the next reaction. It can also be isolated from the reaction mixture according to a conventional method, and can be easily purified by a separation means such as washing, recrystallization, distillation, chromatography and the like.

In another method, compound (18) can also be produced by reduction with about 5.0 to 20.0 mol, preferably about 5.0 to 10.0 mol, of a reducing metal per 1 mol of compound (17).

Examples of the reducing metal include reducing iron, tin, zinc and the like. To promote the reaction, acetic acid, hydrochloric acid, ammonium chloride, calcium chloride or the like can be added.

This reaction is preferably performed using a solvent inert to the reaction. The solvent is not particularly limited as long as the reaction proceeds. Preferable examples thereof include alcohols such as methanol, ethanol, propanol and the like; aromatic hydrocarbons such as benzene, toluene and the like; saturated hydrocarbons such as cyclohexane, hexane and the like; ethers such as tetrahydrofuran, 1,4-dioxane, 1,2-dimethoxyethane and the like; amides such as N,N-dimethylformamide, N,N-dimethylacetamide and the like; ketones such as acetone, methyl ethyl ketone and the like; sulfoxides such as dimethyl sulfoxide and the like; solvents such as aqueous ammonia solution, water and the like or a mixed solvent thereof and the like.

The reaction time is generally 1 hr to 60 hr, preferably 5 hr to 48 hr. The reaction temperature is generally –50° C. to 150° C., preferably 0 to 100° C.

The obtained compound (18) can be used directly as a reaction mixture, or as a crude product, for the next reaction. It can also be isolated from the reaction mixture according to a conventional method, and can be easily purified by a separation means such as washing, recrystallization, distillation, chromatography and the like.

As compound (17), a commercially available reagent can be used, or it can be produced by a method known per se.

<Step B>

In step B, compound (20) is obtained by using about 1.0 to 5.0 mol, preferably about 1.0 to 2.0 mol, of compound (19), about 1.0 to 10.0 mol, preferably about 1.0 to 5.0 mol, of a base, and about 1.0 to 10.0 mol, preferably about 1.0 to 5.0 mol, of an amidation reagent, per 1 mol of compound (18).

Examples of the amidation reagent include 1-ethyl-3-(dimethylaminopropyl)carbodiimide hydrochloride, 0-(benzotriazol-1-yl)-N,N,N',N'-tetramethyluronium hexafluorophosphate (HATU) and the like.

Examples of the base include organic amines such as pyridine, triethylamine, N,N-dimethylaminopyridine, diisopropylethylamine, 1,8-diazabicyclo[5.4.0]undec-7-ene, and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 0.5 hr to 1 week, preferably 3 hr to 24 hr. The reaction temperature is generally –20° C. to 100° C., preferably 0° C. to 80° C.

The obtained compound (20) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (19) may be a commercially available reagent, or can be produced by a method known per se.

<Step C>

In step C, compound (24) is obtained by cyclizing compound (20) in the presence of an acid. When Y is $E^1$, compound (24) is compound (3a"). The amount of the acid to be used is about 0.01 to 100 mol, preferably about 0.1 to 50 mol, relative to compound (20).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide, and the like, and the like. In addition, these acids may be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide, and the like, and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably room temperature to 100° C.

The obtained compound (24) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step D>

In step D, compound (22) is produced by using about 1.0 to 10.0 mol, preferably about 1.0 to 3.0 mol, of compound (21), and about 1.0 to 10.0 mol, preferably about 1.0 to 5.0 mol, of a base, per 1 mol of compound (17).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio. Furthermore, the above-mentioned base may be used as a solvent.

The reaction time is generally 15 min to 60 hr, preferably 15 min to 24 hr. The reaction temperature is generally −20° C. to 150° C., preferably 0° C. to 100° C.

The obtained compound (22) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (21) may be a commercially available reagent, or can be produced by a method known per se.

<Step E>

In step E, compound (23) is produced by reducing compound (22) according to the method shown in the above-mentioned production method 3-2, step A, or a method analogous thereto.

<Step F>

In step F, compound (24) is produced from compound (23) according to the method of the above-mentioned production method 3-2, step C or a method analogous thereto. When Y is $E^1$, compound (24) is compound (3a″).

<Step G>

In step G, the object compound (3b″) is obtained by deprotection of compound (24) wherein Y is HO—W′—, wherein the hydroxy group optionally has a protecting group, as necessary, and subjecting compound (24) to a halogenation or sulfonylation reaction known per se.

In each reaction of the aforementioned schemes, when a starting compound has hydroxy, amino (including —NH—, —NH$_2$), carboxy, carbonyl or mercapto as a substituent, a protecting group generally used in the peptide chemistry and the like may be introduced into these groups. By removing the protecting group as necessary after the reaction, the objective compound can be obtained.

Examples of the hydroxyl-protecting group include $C_{1-6}$ alkyl (e.g., methyl, ethyl, propyl, isopropyl, butyl, tert-butyl), phenyl, trityl, $C_{7-10}$ aralkyl (e.g., benzyl), formyl, $C_{1-6}$ alkyl-carbonyl (e.g., acetyl, propionyl), benzoyl, $C_{7-10}$ aralkyl-carbonyl (e.g., benzylcarbonyl), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkyl (e.g., methyl, ethyl, propyl), $C_{1-6}$ alkoxy (e.g., methoxy, ethoxy, propoxy), nitro and the like.

Examples of the amino-protecting group include formyl, $C_{1-6}$ alkyl-carbonyl (e.g., acetyl, propionyl), $C_{1-6}$ alkoxy-carbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), $C_{7-10}$ aralkyl (e.g., benzyl, 4-methoxybenzyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carboxy-protecting group include $C_{1-6}$ alkyl (e.g., methyl, ethyl, propyl, isopropyl, butyl, tert-butyl), $C_{7-11}$ aralkyl (e.g., benzyl), phenyl, trityl, silyl (e.g., trimethylsilyl, triethylsilyl, dimethylphenylsilyl, tert-butyldimethylsilyl, tert-butyldiethylsilyl, tert-butyldiphenylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carbonyl-protecting group include cyclic acetal (e.g., 1,3-dioxane), acyclic acetal (e.g., di-$C_{1-6}$ alkyl acetal) and the like.

Examples of the mercapto-protecting group include $C_{1-6}$ alkyl, phenyl, trityl, $C_{7-10}$ aralkyl (e.g., benzyl), $C_{1-6}$ alkyl-carbonyl, benzoyl, $C_{7-10}$ aralkyl-carbonyl (e.g., benzylcarbonyl), $C_{1-6}$ alkoxy-carbonyl, $C_{6-14}$ aryloxy-carbonyl (e.g., phenyloxycarbonyl), $C_{7-14}$ aralkyloxy-carbonyl (e.g., benzyloxycarbonyl, 9-fluorenylmethoxycarbonyl), 2-tetrahydropyranyl, $C_{1-6}$ alkylamino-carbonyl (e.g., methylaminocarbonyl, ethylaminocarbonyl) and the like. These groups are optionally substituted by 1 to 3 substituents selected from a halogen atom, $C_{1-6}$ alkyl, $C_{1-6}$ alkoxy, nitro and the like.

The above-mentioned protecting groups can be removed by a method known per se, for example, the method described in Protective Groups in Organic Synthesis, John Wiley & Sons, Inc. (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like are used.

As compound (I) and a prodrug thereof (hereinafter abbreviated as the compound of the present invention) has a superior MCH receptor (particularly, MCH receptor 1) antagonistic action, it is useful as an agent for the prophylaxis or treatment of diseases caused by MCH.

In addition, the compound of the present invention also shows low toxicity (e.g., cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is superior in oral absorbability.

Furthermore, the compound of the present invention is superior in brain transfer function.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of pigmentation due to chloasma, ephelides, sunburn and the like; and further, hyperpigmentation or hypopigmentation for cosmetic purposes.

The compound of the present invention is used as it is or as a pharmaceutical composition (in the present specification, sometimes to be abbreviated as "the medicament of the present invention") formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonic agent, buffer and soothing agent for liquid preparations and the like can be mentioned. Where necessary, additives such as preservatives, antioxidizing agents, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonic agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-hydroxybenzoates, chlorobutanol, benzyl alcohol, phenethyl alcohol, dehydroacetic acid and sorbic acid.

Examples of the antioxidizing agent include sulfite and ascorbic acid.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartame and stevia.

Examples of the adsorbent include porous starch, calcium silicate (trade name: Florite RE), magnesium aluminometasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylene lauryl ether.

Examples of the dosage form of the medicament of the present invention include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucosal patch film), injection (e.g., subcutaneous injection, intravenous injection, intramuscular injection, intraperitoneal injection, drip infusion), transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound in the medicament of the present invention in the pharmaceutical composition is, for example, about 0.1 to 100 wt % of the entire medicament of the present invention.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a pharmaceutically active ingredient (hereinafter sometimes to be referred to as "concomitant drug") that does not adversely influence the compound of the present invention. Examples of such concomitant drug include "therapeutic agent for diabetes", "therapeutic agent for diabetic complications", "anti-obesity agent", "therapeutic agent for hypertension", "therapeutic agent for hyperlipidemia", "antiarteriosclerotic agent", "antithrombotic agent", "diuretic agent", "therapeutic agent for arthritis", "antianxiety agent", "antidepressant", "psychoneurotic agent", "sleep-inducing agent" and the like. These concomitant drugs may be low-molecular-weight compounds, or high-molecular-weight proteins, polypeptides, antibodies, vaccines or the like.

Examples of the above-mentioned "therapeutic agent for diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic agent for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxyl)propyl]oxazole), the compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine. H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NF-κB inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic agent for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic agent for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic agent" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic agent" include heparin (e.g., heparin sodium, heparin calcium, enoxaparin sodium, dalteparin sodium), warfarin (e.g., warfarin potassium), anti-thrombin drugs (e.g., argatroban, dabigatran), FXa inhibitors (e.g., rivaroxaban, apixaban, edoxaban, YM150, the compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic agent for arthritis" include ibuprofen and the like.

Examples of the above-mentioned "antianxiety agent" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, setiptiline), selective serotonin uptake inhibitors (e.g., fluoxetine, fluvoxamine, paroxetine, sertraline, escitalopram), serotoninnoradrenaline uptake inhibitors (e.g., milnacipran, duloxetine, venlafaxine), trazodone, mirtazapine, moclobemide and the like.

Examples of the above-mentioned "psychoneurotic agent" include typical antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing agent" include Ramelteon, GABAergic hypnotics (e.g., brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:
1) administration of a single preparation obtained by simultaneously processing the compound of the present invention and the concomitant drug,
2) simultaneous administration of two kinds of preparations of the compound of the present invention and the concomitant drug, which have been separately produced, by the same administration route, 3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is explained in more detail in the following by referring to Examples, Experimental Examples and Preparation Examples, which are not to be construed as limitative, and can be modified without substantially departing from the scope of the present invention.

In the following Examples, the "room temperature" means generally about 1° C. to about 30° C. In addition, % means weight % unless otherwise indicated.

In the $^1$H NMR spectrum (proton nuclear magnetic resonance spectrum), the chemical shift is expressed in δ value (ppm) and the coupling constant is expressed in Hz.

In the case of a mixed solvent, the ratio is a volume ratio unless otherwise indicated. In addition, % of a solution means the number of grams in 100 mL of the solution.

The abbreviations mentioned below are used in the following Examples.
s: singlet
d: doublet
t: triplet
q: quartet
dd: double doublet
dt: double triplet
tt: triple triplet
m: multiplet
br: broad
J: coupling constant
DMSO-$d_6$: dimethyl sulfoxide-$d_6$
$^1$H NMR: proton nuclear magnetic resonance
MS(ESI): mass spectrometry (electrospray ionization)
MeOH: methanol
EtOH: ethanol
Et$_2$O: diethyl ether
POCl$_3$: phosphorus oxychloride
AcOEt: ethyl acetate
CH$_3$CN: acetonitrile
DMSO: dimethyl sulfoxide
IPE: diisopropyl ether
IPA: isopropanol
THF: tetrahydrofuran
DMF: N,N-dimethylformamide
DMA: N,N-dimethylacetamide
DCM: dichloromethane
K$_2$CO$_3$: potassium carbonate
NaHCO$_3$: sodium hydrogen carbonate
NH$_4$Cl: ammonium chloride
AcOH: acetic acid
TFA: trifluoroacetic acid
MgSO$_4$: magnesium sulfate
MS-4A: molecular sieves 4A
N$_2$: nitrogen
HPLC: high performance liquid chromatography Example 1

2-(4-Chlorophenyl)-5-(2-cyclopropyl-3-methylimidazo[1,2-a]pyridin-6-yl)furo[3,2-c]pyridin-4(5H)-one A) (2-Cyclopropyl-3-methylimidazo[1,2-a]pyridin-6-yl)boronic acid To a solution of 2-cyclopropyl-6-iodo-3-methylimidazo[1,2-a]pyridine (742 mg) in THF (25 mL) was added n-butyllithium (1.6 M in hexane, 6.2 mL) at −78° C. The mixture was stirred at −78° C. under a nitrogen atmosphere for 30 min. Boric acid triisopropyl ester (0.86 mL) was added to the obtained mixture at −78° C. The mixture was stirred at −78° C. for 30 min and then at room temperature for 3 hr. The mixture was poured into 1 N sodium hydroxide at 0° C. and washed with ethyl acetate. The obtained aqueous layer was neutralized with 1 N hydrochloric acid to pH 7.0 and extracted with ethyl acetate/2-propanol. The obtained organic layer was washed with brine, dried over magnesium sulfate and concentrated in vacuo. The resulting solid was washed with ethyl acetate/methanol to give the title compound (176 mg) as a yellow solid.
MS (ESI+): [M+H]+217.2.

B) 2-(4-Chlorophenyl)-5-(2-cyclopropyl-3-methylimidazo[1,2-a]pyridin-6-yl)furo[3,2-c]pyridin-4(5H)-one A mixture of 2-(4-chlorophenyl)furo[3,2-c]pyridin-4(5H)-one (100 mg), (2-cyclopropyl-3-methylimidazo[1,2-a]pyridin-6-yl)boronic acid (106 mg), copper(II) acetate (4.99 mg), pyridine (0.066 mL), MS-4A (48.9 mg) and DMF (5.0 mL) was stirred at room temperature for 4 hr and at 50° C. overnight. After filtration of the obtained mixture through Celite, the filtrate was poured into 1 N hydrochloric acid and extracted with ethyl acetate. The obtained organic layer was washed with saturated aqueous sodium hydrogen carbonate solution and brine, dried over magnesium sulfate and concentrated in vacuo. The obtained solid was washed with ethanol to give the title compound (10.0 mg) as a pale brown solid.
$^1$H NMR (300 MHz, DMSO-$d_6$) δ 0.84-0.99 (4H, m), 2.04-2.14 (1H, m), 6.94 (1H, dd, J=7.6, 0.8 Hz), 7.21 (1H, dd, J=9.4, 1.9 Hz), 7.49 (1H, d, J=9.4 Hz), 7.53-7.59 (2H, m), 7.66 (1H, s), 7.75 (1H, d, J=7.6 Hz), 7.88-7.96 (2H, m), 8.48 (1H, d, J=1.5 Hz). (DMSO region includes 3H of methyl group on the 7 position of imidazopyridine ring.)
MS (ESI+): [M+H]+416.1.

Example 2

2-(4-Chlorophenyl)-5-(2-cyclopropyl-1-methyl-1H-benzimidazol-6-yl)furo[3,2-c]pyridin-4(5H)-one A) 5-Bromo-N-methyl-2-nitroaniline To a solution of 4-bromo-2-fluoro-1-nitrobenzene (25 g) in ethanol (100 mL) was added methylamine (40% in methanol, 34.8 mL) at room temperature, and the mixture was stirred for 1 hr. The obtained mixture was cooled to 0° C., and the resulting precipitate was collected by filtration and washed with ice-cooled ethanol and diisopropyl ether. The obtained solid was dried to give the title compound (24.8 g) as a yellow solid.

$^1$H NMR (300 MHz, DMSO-d$_6$): δ 2.95 (3H, d, J=4.9 Hz), 6.83 (1H, dd, J=9.1, 1.9 Hz), 7.17 (1H, d, J=1.9 Hz), 7.98 (1H, d, J=9.1 Hz), 8.23 (1H, brs).

B)
6-Bromo-2-cyclopropyl-1-methyl-1H-benzimidazole

A mixture of 5-bromo-N-methyl-2-nitroaniline (4.2 g), zinc (5.9 g), ammonium chloride (9.7 g) and methanol (50 mL) was stirred at room temperature for 3 hr. After removing the methanol, the obtained mixture was neutralized with saturated aqueous sodium hydrogen carbonate solution and extracted with ethyl acetate. The obtained organic layer was washed with water and brine, dried over magnesium sulfate and concentrated in vacuo. The obtained residue was dissolved in phosphorus oxychloride (1.68 mL), and cyclopropanecarboxylic acid (2.86 mL) was added to the solution at room temperature. The obtained mixture was stirred at 120° C. for 3 hr. After cooling the reaction mixture to 0° C., ice water and saturated aqueous sodium hydrogen carbonate solution were carefully added dropwise, and the mixture was extracted with ethyl acetate. The obtained organic layer was washed with brine, dried over magnesium sulfate, and concentrated in vacuo. The obtained residue was dissolved in 1 N hydrochloric acid and washed with ethyl acetate. The aqueous layer was basified with 4 N sodium hydroxide and extracted with ethyl acetate. The obtained organic layer was washed with brine, dried over magnesium sulfate, and concentrated in vacuo to give the title compound (3.3 g) as a brown solid.

$^1$H NMR (300 MHz, DMSO-d$_6$): δ 0.95-1.14 (4H, m), 2.23 (1H, tt, J=7.9, 5.1 Hz), 3.83 (3H, s), 7.24 (1H, dd, J=8.5, 2.1 Hz), 7.41 (1H, d, J=8.7 Hz), 7.75 (1H, d, J=1.9 Hz).

C) 2-(4-Chlorophenyl)-5-(2-cyclopropyl-1-methyl-1H-benzimidazol-6-yl)furo[3,2-c]pyridin-4(5H)-one A mixture of 2-(4-chlorophenyl)furo[3,2-c]pyridin-4 (5H)-one (100 mg), 6-bromo-2-cyclopropyl-1-methyl-1H-benzimidazole (123 mg), N,N'-dimethylethylenediamine (0.043 mL), copper(I) iodide (78.0 mg), potassium carbonate (169 mg) and DMSO (3.0 mL) was stirred at 190° C. for 1 hr under microwave irradiation. The reaction mixture was purified by silica gel column chromatography (NH, ethyl acetate/hexane), and the obtained solid was washed with ethyl acetate to give the title compound (37.3 mg) as a pale red solid.

$^1$H NMR (400 MHz, DMSO-d$_5$) δ 1.02-1.14 (4H, m), 2.28 (1H, t, J=4.8 Hz), 3.87 (3H, s), 6.88 (1H, d, J=7.4 Hz), 7.14 (1H, d, J=8.2 Hz), 7.51-7.65 (5H, m), 7.67 (1H, d, J=7.4 Hz), 7.92 (2H, d, J=8.3 Hz).

MS (ESI+): [M+H]+416.1.

Example 3

2-(5-Chloropyridin-2-yl)-5-(2-cyclopropyl-3-methyl-imidazo[1,2-a]pyridin-6-yl)furo[3,2-c]pyridin-4 (5H)-one A)
N-(5-Iodopyridin-2-yl)-4-methylbenzenesulfonamide A mixture of 5-iodopyridin-2-amine (25.5 g), 4-methylbenzene-1-sulfonyl chloride (23.2 g) and pyridine (250 mL) was stirred at 100° C. overnight. The reaction mixture was poured into water (1.2 L) and stirred. The resulting solid was collected by filtration. The obtained solid was washed with water and diethyl ether and dried in vacuo to give the title compound (37.4 g) as a white solid.

MS (ESI+): [M+H]+374.9.

B) N-(1-(1-Cyclopropyl-1-oxopropan-2-yl)-5-iodopyridin-2(1H)-ylidene)-4-methylbenzenesulfonamide To a solution of N-(5-iodopyridin-2-yl)-4-methylbenzenesulfonamide (33.1 g) in DMF (400 mL) was added sodium hydride (60% oil dispersion, 3.89 g) at 0° C., and the mixture was stirred at room temperature for 30 min. Then 2-bromo-1-cyclopropylpropan-1-one (23.5 g) was added to the obtained mixture, and the mixture was stirred at room temperature overnight. The reaction mixture was poured into water and extracted with ethyl acetate. The obtained organic layer was washed with brine, dried over magnesium sulfate, and concentrated in vacuo. The resulting solid was suspended in diisopropyl ether, the suspension was stirred for 1 hr, and the solid was collected by filtration. The obtained solid was dissolved in ethyl acetate (1100 mL) at 70° C., and hexane (400 mL) was dropwise added at 60° C. The mixture was allowed to cool to room temperature overnight. The resulting precipitate was collected by filtration, washed with hexane/ethyl acetate (1/1) 3 times, and dried to give the title compound (30.5 g) as a white solid.

MS (ESI+): [M+H]+470.9.

C) 2-Cyclopropyl-6-iodo-3-methylimidazo[1,2-a]pyridine

To a solution of N-(1-(1-cyclopropyl-1-oxopropan-2-yl)-5-iodopyridin-2(1H)-ylidene)-4-methylbenzenesulfonamide (30.5 g) in THF (300 mL) was added trifluoroacetic anhydride (18.3 mL) dropwise, and the mixture was stirred for 3 hr. The resulting precipitate was collected by filtration, and washed with diethyl ether to give a salt of the title compound as a white solid. The obtained solid was dissolved in 1 N sodium hydroxide, and the solution was extracted with ethyl acetate/THF. Then the organic layer was washed with brine, dried over sodium sulfate and concentrated in vacuo. The obtained solid was washed with diisopropyl ether to give the title compound (17.7 g) as a yellow solid.

MS (ESI+): [M+H]+299.0.

D) 3-(5-Bromo-2-furyl)acryloyl azide

To a solution of 3-(5-bromo-2-furyl)acrylic acid (41.5 g) in acetonitrile (200 mL) were added triethylamine (23.0 g) and ethyl chloroformate (26.1 g). The mixture was stirred at room temperature for 30 min. To the obtained mixture was added a saturated aqueous solution of sodium azide (18.7 g) at 0° C. and the mixture was stirred at room temperature for 5 hr. The reaction mixture was filtered, and the obtained solid was washed with water. The solid was recrystallized from dichloromethane to give the title compound (20.7 g) as white solid.

$^1$H NMR (400 MHz, DMSO-d$_6$) δ 6.23 (1H, d, J=15.2 Hz), 6.82 (1H, d, J=3.2 Hz), 7.13 (1H, d, J=3.6 Hz), 7.51 (1H, d, J=15.6 Hz).

E) 2-Bromofuro[3,2-c]pyridin-4(5H)-one

A mixture of 3-(5-bromo-2-furyl)acryloyl azide (20.7 g), diphenyl ether (200 mL) and tributylamine (16 mL) was stirred at 220-230° C. for 30 min under a nitrogen atmosphere. The reaction mixture was allowed to cool to room temperature, and tert-butyl methyl ether (200 mL) was added thereto. The resulting solid was collected by filtration. The obtained solid was purified by silica gel column chromatography (hexane, then ethyl acetate/THF), followed by HPLC (C18, mobile phase: water/acetonitrile (including 0.1% TFA)). To the obtained fraction was added a saturated aqueous sodium hydrogen carbonate solution, and the mixture was extracted with ethyl acetate. The extract was dried over anhydrous magnesium sulfate, concentrated in vacuo, and recrystallized from ethyl acetate to give the title compound (7.00 g) as a white solid.

MS (ESI+): [M+H]+213.8.

F) 2-(5-Chloropyridin-2-yl)furo[3,2-c]pyridin-4(5H)-one

A mixture of 2-bromofuro[3,2-c]pyridin-4(5H)-one (200 mg), lithium 1-(5-chloropyridin-2-yl)-4-methyl-2,6,7-trioxa-1-borabicyclo[2.2.2]octan-1-uide (462 mg), palladium (II) acetate (21.0 mg), copper(I) iodide (178 mg), triphenylphosphine (49.0 mg) and DMA (1.0 mL) was heated at 250° C. for 30 min under microwave irradiation. The reaction mixture was purified by silica gel column chromatography (NH, methanol/ethyl acetate), and the obtained solid was washed with diisopropyl ether to give the title compound (69.0 mg) as a white solid.

MS (ESI): [M+H]+247.0.

G) 2-(5-Chloropyridin-2-yl)-5-(2-cyclopropyl-3-methylimidazo[1,2-a]pyridin-6-yl)furo[3,2-c]pyridin-4(5H)-one A mixture of 2-(5-chloropyridin-2-yl)furo[3,2-c]pyridin-4(5H)-one (69.0 mg), 2-cyclopropyl-6-iodo-3-methylimidazo[1,2-a]pyridine (100 mg), N,N'-dimethylethylenediamine (0.030 mL), copper(I) iodide (53.3 mg), potassium carbonate (116 mg) and DMSO (3.0 mL) was heated at 220° C. for 1 hr under microwave irradiation. The reaction mixture was purified by silica gel column chromatography (NH, ethyl acetate/hexane), and the obtained solid was washed with ethyl acetate to give the title compound (2.30 mg) as a pale red solid.

$^1$H NMR (400 MHz, DMSO-$d_6$) δ 0.81-1.01 (4H, brs), 1.99-2.19 (1H, brs), 6.88-7.08 (1H, brs), 7.13-7.33 (1H, brs), 7.39-7.59 (1H, d, J=4.8 Hz), 7.57-7.77 (1H, brs), 7.71-7.91 (1H, brs), 7.89-8.01 (1H, brs), 7.97-8.17 (1H, brs), 8.39-8.59 (1H, brs), 8.62-8.82 (1H, brs). (DMSO region includes 3H of methyl group on the 7 position of imidazopyridine ring.)

MS (ESI+): [M+H]+417.1.

Example 4

2-(4-Chlorophenyl)-5-(2-((1RS,2SR)-2-(2-hydroxypropan-2-yl)cyclopropyl)-1-methyl-1H-benzimidazol-6-yl)furo[3,2-c]pyridin-4(5H)-one A) (1RS,2SR)-2-(Methoxycarbonyl)cyclopropanecarboxylic acid 3-Oxabicyclo[3.1.0]hexane-2,4-dione (766 mg) was added to methanol (10 mL) at 0° C. After addition of triethylamine (0.953 mL), the mixture was stirred at room temperature for 1 hr. The solvent was evaporated. The residue was dissolved in ethyl acetate, washed with 1 N hydrochloric acid and brine, dried over magnesium sulfate and concentrated in vacuo to give the title compound (460 mg) as a colorless oil.

$^1$H NMR (300 MHz, CHLOROFORM-d) δ 1.34 (1H, dt, J=8.5, 4.9 Hz), 1.70 (1H, dt, J=6.8, 4.9 Hz), 2.02-2.22 (2H, m), 3.72 (3H, s).

B) Methyl (1RS,2SR)-2-(6-bromo-1-methyl-1H-benzimidazol-2-yl)cyclopropanecarboxylate O-(7-Azabenzotriazol-1-yl)-N,N,N',N'-tetramethyluronium hexafluorophosphate (554 mg) was added to a solution of 4-bromo-$N^2$-methylbenzene-1,2-diamine (279 mg), diisopropylethylamine (0.727 mL) and (1RS,2SR)-2-(methoxycarbonyl)cyclopropanecarboxylic acid (200 mg) in DMF (5 mL) at room temperature. The mixture was stirred for 1 hr. Water was added to the reaction mixture, and the mixture was extracted with ethyl acetate. The obtained organic layer was washed with water and brine, dried over magnesium sulfate and concentrated in vacuo. The obtained residue was dissolved in acetic acid (5 mL), and the mixture was stirred at 80° C. for 1 hr. After concentration of the reaction mixture, saturated sodium hydrogen carbonate was added to the residue, and the mixture was extracted with ethyl acetate. The obtained organic layer was washed with water and brine, dried over magnesium sulfate and concentrated in vacuo. The obtained residue was purified by silica gel column chromatography (methanol/ethyl acetate) to give the title compound (80 mg) as a pale brown solid.

MS (ESI+): [M+H]+309.1.

$^1$H NMR (400 MHz, DMSO-$d_6$) δ 1.55 (1H, dt, J=8.4, 4.3 Hz), 1.72-1.80 (1H, m), 2.26-2.36 (1H, m), 2.74 (1H, q, J=8.4 Hz), 3.41 (3H, s), 3.72 (3H, s), 7.28 (1H, d, J=8.5 Hz), 7.49 (1H, d, J=8.5 Hz), 7.76 (1H, s).

C) 2-((1RS,2SR)-2-(6-Bromo-1-methyl-1H-benzimidazol-2-yl)cyclopropyl)propan-2-ol Methylmagnesium chloride (3.0 M in THF, 0.69 mL) was added to a solution of methyl (1RS,2SR)-2-(6-bromo-1-methyl-1H-benzimidazol-2-yl)cyclopropanecarboxylate (80 mg) in THF (2 mL) at 0° C., and the mixture was stirred at room temperature for 3 hr. 1 N Hydrochloric acid was added to the reaction mixture, and the mixture was extracted with ethyl acetate. The obtained organic layer was washed with saturated aqueous sodium hydrogen carbonate solution and brine, dried over magnesium sulfate and concentrated in vacuo. The obtained residue was purified by silica gel column chromatography (ethyl acetate/hexane) to give the title compound (34 mg) as a white solid.

$^1$H NMR (300 MHz, CHLOROFORM-d) δ 1.28-1.35 (5H, m), 1.46-1.63 (4H, m), 1.92-2.03 (1H, m), 3.80 (3H, s), 7.28-7.35 (1H, m), 7.38-7.50 (2H, m).

MS (ESI+): [M+H]+309.2.

D) 2-(4-Chlorophenyl)-5-(2-((1RS,2SR)-2-(2-hydroxypropan-2-yl)cyclopropyl)-1-methyl-1H-benzimidazol-6-yl)furo[3,2-c]pyridin-4(5H)-one A mixture of 2-(4-chlorophenyl)furo[3,2-c]pyridin-4(5H)-one (100 mg), 2-((1RS,2SR)-2-(6-bromo-1-methyl-1H-benzimidazol-2-yl)cyclopropyl)propan-2-ol (151 mg), N,N'-dimethylethylenediamine (0.043 mL), copper(I) iodide (78.0 mg), potassium carbonate (169 mg) and DMSO (3.0 mL) was heated at 190° C. for 1 hr under microwave irradiation. The reaction mixture was purified by silica gel column chromatography (NH, ethyl acetate/hexane), and the obtained solid was washed with ethyl acetate to give the title compound (37.9 g) as a pale red solid.

$^1$H NMR (400 MHz, CHLOROFORM-d) δ 1.31 (3H, s), 1.34-1.43 (4H, m), 1.50-1.70 (2H, m), 1.94-2.11 (1H, m), 3.84 (3H, s), 6.66 (1H, d, J=7.5 Hz), 6.89 (1H, brs), 7.17 (1H, d, J=8.4 Hz), 7.23-7.28 (1H, m), 7.36 (1H, d, J=7.4 Hz), 7.39-7.46 (3H, m), 7.67 (1H, d, J=8.4 Hz), 7.72 (2H, d, J=8.4 Hz).

MS (ESI+): [M+H]+474.1.

| | | |
|---|---|---|
| (3) | Lactose | 19 mg |
| (4) | Magnesium stearate | 1 mg |
| | Total | 60 mg |

(1), (2), (3) and (4) are mixed and filled in a gelatin capsule.

TABLE 1

| Ex. | IUPAC name | Structure | MS |
|---|---|---|---|
| 1 | 2-(4-chlorophenyl)-5-(2-cyclopropyl-3-methylimidazo[1,2-a]pyridin-6-yl)furo[3,2-c]pyridin-4(5H)-one | 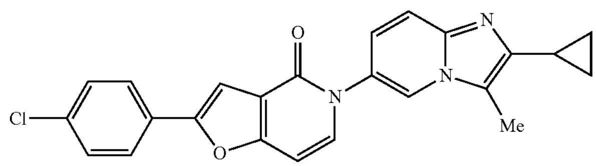 [SMILES: Cc1c(C2CC2)nc2ccc(-n3ccc4oc(-c5ccc(Cl)cc5)cc4c3=O)cn12] | 416.1 |
| 2 | 2-(4-chlorophenyl)-5-(2-cyclopropyl-1-methyl-1H-benzimidazol-6-yl)furo[3,2-c]pyridin-4(5H)-one | 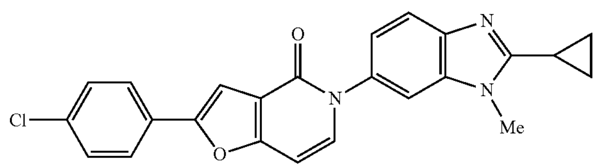 [SMILES: Cn1c(C2CC2)nc2ccc(-n3ccc4oc(-c5ccc(Cl)cc5)cc4c3=O)cc21] | 416.1 |
| 3 | 2-(5-chloropyridin-2-yl)-5-(2-cyclopropyl-3-methylimidazo[1,2-a]pyridin-6-yl)furo[3,2-c]pyridin-4(5H)-one | 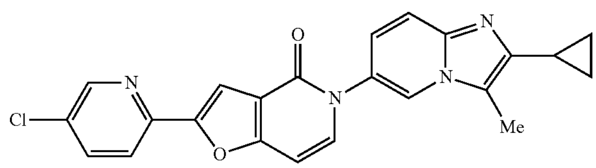 [SMILES: Cc1c(C2CC2)nc2ccc(-n3ccc4oc(-c5ccc(Cl)cn5)cc4c3=O)cn12] | 417.1 |
| 4 | 2-(4-chlorophenyl)-5-(2-((1RS,2SR)-2-(2-hydroxypropan-2-yl)cyclopropyl)-1-methyl-1H-benzimidazol-6-yl)furo[3,2-c]pyridin-4(5H)-one | 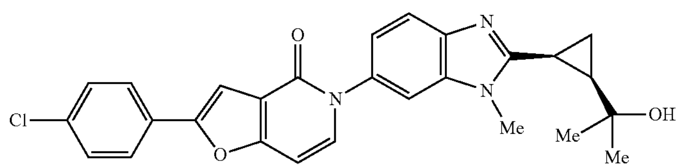 [SMILES: Cn1c([C@H]2C[C@H]2C(C)(C)O)nc2ccc(-n3ccc4oc(-c5ccc(Cl)cc5)cc4c3=O)cc21] | 474.1 |

Preparation Example 1

| | | |
|---|---|---|
| (1) | Compound of Example 1 | 50 mg |
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Calcium carboxymethylcellulose | 20 mg |
| | Total | 120 mg |

The above-mentioned (1) to (6) are mixed according to a conventional method and the mixture is tableted by a tableting machine to give a tablet.

Preparation Example 2

Production of Capsule

| | | |
|---|---|---|
| (1) | Compound of Example 1 | 30 mg |
| (2) | Crystalline cellulose | 10 mg |

Experimental Example 1

Determination of Human MCH Receptor 1 (MCHR1) Binding Inhibitory Activity of Test Compound Using Binding Assay 1. Preparation of Membrane Fraction Using human MCHR1(=SLC-1 receptor)-expressing CHO cell clone 57 described in WO01/82925, MCHR1-expressing CHO cellular membrane fractions were prepared by the following method.

In phosphate buffered saline (pH 7.4) supplemented with 5 mM EDTA (ethylenediaminetetraacetic acid) were respectively suspended human MCHR1-expressing CHO cells ($1\times10^8$ cells) and centrifuged. Homogenate buffer (10 mL, 10 mM NaHCO$_3$, 5 mM EDTA, pH 7.5, 0.5 mM PMSF (phenylmethylsulfonyl fluoride), 20 mg/L leupeptin, 4 mg/L E-64, 1 mg/L pepstatin A) was added to the pellets of the cells and, using Polytron Homogenizer, the mixture was homogenated. The supernatant obtained after centrifugation at 400×g for 10 min was further centrifuged at 100,000×g for 1 hr to give precipitate of the membrane fraction. The precipitate were suspended in 2 mL of assay buffer [20 mM Tris-HCl (pH 7.5), 5 mM EDTA, 0.5 mM PMSF, 20 mg/L leupeptin, 4 mg/L E-64, 1 mg/L pepstatin A]. The membrane fractions were suspended in assay buffer to a protein concentration of 2 mg/mL, and after dispensing, preserved at −80° C. and used upon thawing each time when in use.

2. Binding Assay

The MCHR1 ligand binding inhibitory activity of the test compound was determined as follows.

An MCHR1-expressing CHO cellular membrane fraction (173 μL) diluted with an assay buffer was dispensed to a 96 well polypropylene plate (3363, Corning). DMSO solution (2 μL), 33 μM cold MCH(1-19) diluted with DMSO solution (2 μL), or a test compound solution diluted with DMSO solution to various concentrations (2 μL) was added, and lastly, [$^{125}$I]-MCH(4-19) diluted with assay buffer (hereinafter, sometimes to be referred to as "hot MCH", 25 μL) was added to each well. The mixture was reacted with stirring at room temperature for 1 hr, and the plate was set on FilterMate Harvester (PerkinElmer). Using a treating glass filter plate (GF/C, PerkinElmer) with polyethyleneimine, which had been previously set, the plate was suction-filtered and washed three times with washing buffer (50 mM Tris-HCl buffer pH 7.5). The glass filter plate was dried, MicroScinti0 (PerkinElmer) was added at 25 μL/well, and the resulting radioactivity was measured by TopCount liquid scintillation counter (PerkinElmer). The binding inhibition rate of the test compound was calculated by the following formula.

Binding inhibition (%)=100−(radioactivity upon addition of test compound and hot MCH−radioactivity upon addition of cold MCH and hot MCH solution)/(radioactivity upon addition of DMSO solution and hot MCH−radioactivity upon addition of cold MCH and hot MCH solution)×100

The binding inhibition rates (%) of test compounds (0.1 μM) as measured using human MCHR1-expressing CHO cell are shown in Table 2.

TABLE 2

| compound No. | Binding inhibition rate % (0.1 μM) |
| --- | --- |
| Example 1 | 100 |
| Example 2 | 79 |
| Example 3 | 74 |
| Example 4 | 91 |

As is clear from Table 2, the compound of the present invention has a superior MCH receptor 1 binding inhibitory activity.

Experimental Example 2

Measurement of MCH Receptor 1 Antagonistic Activity of Test Compound Using $Ca^{2+}$ Mobilization Assay Using an expression vector plasmid introduced with human MCHR1 gene for expression in animal cells, human MCHR1 gene was introduced into CHO cells (CHO dhfr$^-$) by Lipofectamine LTX (Invitrogen). The cells were cultured in selection MEMα medium [445 mL of MEMα medium without nucleic acid and added with 5 mL of Penicillin-Streptomycin (Invitrogen) and 50 mL of dialyzed fetal bovine serum]. Colony 24 clones grown in the selection medium, which were human MCHR1 gene-expressing CHO cell candidates, were selected. From these clones, clone #4 which showed the highest response to the change of $Ca^{2+}$ concentration on stimulation by the addition of 25 nM ligand MCH(4-19) was selected by $Ca^{2+}$ mobilization assay. In the following test, this human MCHR1-expressing CHO cell (clone #4) was used. An integrated dispensing function fluorometer (CellLux, PerkinElmer) was used for $Ca^{2+}$ mobilization assay. The CHO cells were sown in a 96 well plate (type 3904, Corning) with a black wall and clear well bottom at a density of 20000 cells/well, and cultured in an incubator for about 24 hr at 5% $CO_2$, 37° C. The medium was removed, and the cells were washed with phosphate buffered saline (PBS). A $Ca^{2+}$ indicator dye reagent (DOJINDO LABORATORIES, Ca screening no-wash kit Fluo4) was added at 100 μL/well, and the dye was allowed to penetrate into the cell for 30 min in an incubator at 5% $CO_2$, 37° C. The plate was set on a plate reader. First, a test compound solution diluted with an assay buffer [10 mM HEPES (pH 7.4), 1× assay buffer containing 0.1% BSA (DOJINDO LABORATORIES, attached to Ca screening no-wash kit Fluo4)] or DMSO solution was added at 50 μL/well, and then ligand MCH (4-19) peptide (final concentration 2 nM) diluted with assay buffer or DMSO was added at 50 μL/well, during which changes in intracellular fluorescence were measured at 2 second intervals. The antagonistic activity of the test compound was calculated by the following formula and shown as an inhibition rate (%) wherein the intracellular fluorescence activity resulting from the stimulation by the addition of ligand MCH (4-19) peptide was 100% and that of the well added with DMSO solution alone was 0%.

inhibitory rate (%)=100−[fluorescence activity upon addition of test compound and MCH(4-19)peptide solution−fluorescence activity upon addition of DMSO solution only]/[fluorescence activity upon addition of DMSO solution and MCH(4-19)peptide solution−fluorescence activity upon addition of DMSO solution only]×100

The inhibition rates (%) of test compounds (0.1 μM) as antagonist activity measured using human MCHR1-expressing CHO cells (clone #4) are shown in the following Table 3.

TABLE 3

| compound No. | Inhibition rate % (0.1 μM) |
| --- | --- |
| Example 1 | 82 |
| Example 2 | 70 |
| Example 3 | 92 |

As is clear from Table 3, the compound of the present invention has a superior MCH receptor 1 antagonistic action.

INDUSTRIAL APPLICABILITY

Compound (I) has a melanin-concentrating hormone (MCH) receptor antagonistic action, and is low toxic. Therefore, the compound is highly useful as an anorexigenic agent and an agent for the prophylaxis or treatment of obesity and the like.

The present invention is based on U.S. patent application No. 61/645,164, the contents of which are incorporated by reference in full herein.

The invention claimed is:
1. A compound of formula (I),

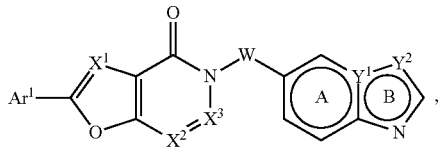

wherein
ring AB is further substituted by;
(1) a $C_{1-6}$ alkyl group, and
(2) a cyclopropyl group optionally substituted by a $C_{1-6}$ alkyl group optionally substituted by 1 to 3 hydroxy groups;
$Ar^1$ is a phenyl group, a pyridyl group, a thienyl group or a furyl group, each of which is optionally substituted by 1 to 3 halogen atoms;
$X^1$ is $CR^1$;
$X^2$ and $X^3$ are each CH;
one of $Y^1$ and $Y^2$ is a carbon atom and the other is a nitrogen atom;
W is a bond; and
$R^1$ is a hydrogen atom or a salt thereof.

2. The compound according to claim 1, wherein $Ar^1$ is a phenyl group or a pyridyl group, each of which is optionally substituted by 1 to 3 halogen atoms, or a salt thereof.

3. A pharmaceutical compostition comprising the compound according to claim 1, or a salt thereof, and a pharmacologically acceptable carrier.

4. A method of antagonizing a melanin-concentrating hormone receptor in a mammal, comprising administering an effective amount of the compound according to claim 1 or a salt thereof to the mammal.

5. A method of suppressing food intake in a mammal, comprising administering an effective amount of the compound according to claim 1 or a salt thereof to the mammal.

6. A method for the prophylaxis or treatment of obesity in a mammal, comprising administering an effective amount of the compound according to claim 1 or a salt thereof to the mammal.

7. The compound according to claim 1, which is 2-(4-chlorophenyl)-5-(2-cyclopropyl-3-methylimidazo[1,2-a]pyridin-6-yl)furo[3,2-c]pyridin-4(5H)-one or a salt thereof.

8. The compound according to claim 1, which is 2-(4-chlorophenyl)-5-(2-cyclopropyl-1-methyl-1H-benzimidazol-6-yl)furo[3,2-c]pyridin-4(5H)-one or a salt thereof.

9. The compound according to claim 1, which is 2-(5-chloropyridin-2-yl)-5-(2-cyclopropyl-3-methylimidazo[1,2-a]pyridin-6-yl)furo[3,2-c]pyridin-4(5H)-one or a salt thereof.

10. The compound according to claim 1, which is 2-(4-chlorophenyl)-5-(2-((1RS,2 SR)-2-(2-hydroxypropan-2-yl)cyclopropyl)-1-methyl-1H-benzimidazol-6-yl)furo[3,2-c]pyridin-4(5H)-one or a salt thereof.

* * * * *